(12) United States Patent
Nirogi et al.

(10) Patent No.: US 8,404,720 B2
(45) Date of Patent: Mar. 26, 2013

(54) ARYL SULFONAMIDE AMINE COMPOUNDS AND THEIR USE AS 5-HT6 LIGANDS

(75) Inventors: Ramakrishna Nirogi, Hyderabad (IN); Anil Karbhari Shinde, Hyderabad (IN); Rama Sastri Kambhampati, Hyderabad (IN); Pradeep Jayarajan, Hyderabad (IN); Gopinadh Bhyrapuneni, Hyderabad (IN); Venkateswarlu Jasti, Hyderabad (IN)

(73) Assignee: Suven Life Sciences Limited, Hyderabad (IN)

( * ) Notice: Subject to any disclaimer, the term of this patent is extended or adjusted under 35 U.S.C. 154(b) by 16 days.

(21) Appl. No.: 13/063,436

(22) PCT Filed: Mar. 3, 2009

(86) PCT No.: PCT/IN2009/000145
§ 371 (c)(1),
(2), (4) Date: May 31, 2011

(87) PCT Pub. No.: WO2010/032258
PCT Pub. Date: Mar. 25, 2010

(65) Prior Publication Data
US 2012/0129816 A1 May 24, 2012

(30) Foreign Application Priority Data
Sep. 17, 2008 (IN) .......................................... 2264/08

(51) Int. Cl.
*A61K 31/4468* (2006.01)
*C07D 211/58* (2006.01)
(52) U.S. Cl. .................................. 514/329; 546/223
(58) Field of Classification Search .................. None
See application file for complete search history.

(56) References Cited

U.S. PATENT DOCUMENTS
2002/0019531 A1 2/2002 Kitazawa et al.
2007/0197533 A1* 8/2007 Zhou et al. .................... 514/241

FOREIGN PATENT DOCUMENTS
| WO | 9827081 | 6/1998 |
| WO | 9902502 | 1/1999 |
| WO | 9937623 | 7/1999 |
| WO | 9942465 | 8/1999 |
| WO | 0063203 | 10/2000 |
| WO | 0132646 | 5/2001 |
| WO | 0236562 | 5/2002 |
| WO | 02060871 | 8/2002 |
| WO | 02098857 | 12/2002 |
| WO | 02098878 | 12/2002 |
| WO | 03013510 | 2/2003 |
| WO | 03065046 | 8/2003 |
| WO | 03066056 | 8/2003 |
| WO | 03080580 | 10/2003 |
| WO | 2004048328 | 6/2004 |
| WO | 2004048330 | 6/2004 |
| WO | 2004048331 | 6/2004 |
| WO | 2004055026 | 7/2004 |
| WO | 2005013974 | 2/2005 |
| WO | 2005058858 | 6/2005 |

OTHER PUBLICATIONS

Shafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Lohani, S. (2006) Understanding nucleation process in the crystallization of polymorphs. (Doctoral dissertataion). Retrieved from ProQuest Dissertataions and Thesis. (Assession Order No. AAT3234930).*
Morissette, S. L., Almarsson, O., Peterson, M. L., Remenar, J. F., Read, M. J., Lemmo, A. V., Ellis, S., Cima, M. J., Gardner, C. R. High-throughput crystallization: polymorphs, salts, co-crystals, and solvates of pharmaceutical solids. Advanced Drug Delivery Reviews. Feb. 2004, 56, 275-300.*
RN: 1047792-50-6 (Registry), Entered date: Sep. 9, 2008, Chemical Library from Albany Molecular research Inc. (AMRI), STN files: CHEMCATS.*
RN: 1054134-28-9 (REGISTRY), Entered date: Sep. 28, 2008, Chemica library from Ambinter, STN files: CHEMCATS.*
Chemical Abstract Registry No. 685115-53-1, indexed in the Registry File on STN CAS Online May 24, 2004.*
Liu, K. G., Robichaud, A. J. 5-HT6 Antagonists as Potential Treatment for Cognitive Dysfunction. Drug Development Research, 2009, 70, 145-168.*
European Patent Office (International Preliminary Examining Authority), International Preliminary Report on Patentability, PCT/IN2009/000145, Aug. 27, 2010, Munich Germany.
Demchyshyn, L L., ALX-1161: Pharmacological Properties of a Potent and Selective 5-HT6 Receptor Antagonist, Society for Neuroscience, Abstract Archive: 2000-2005, Neuroscience 2001 Abstract, Nov. 12, 2001.
Jane C. Bentley, et al, Investigation of stretching behaviour induced by the selective 5-HT6 receptor antagonist, Ro 04-6790, in rats, British Journal of Pharmacology (1999), pp. 1537-1542.

(Continued)

*Primary Examiner* — Jason M Nolan
*Assistant Examiner* — Po-Chih Chen
(74) *Attorney, Agent, or Firm* — IpHorgan Ltd

(57) ABSTRACT

The present invention relates to novel aryl sulfonamide amine compounds of the formula (I), their tautomeric forms, their stereoisomers, their polymorphs, their pharmaceutically acceptable salts, their pharmaceutically acceptable solvates described herein and pharmaceutically acceptable compositions containing them.

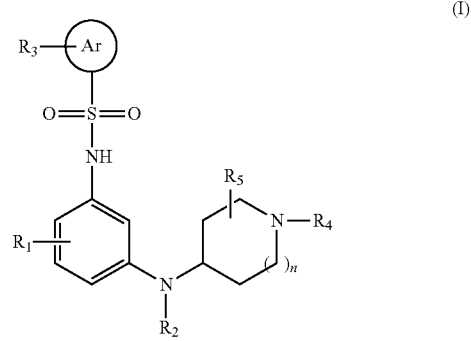

(I)

11 Claims, No Drawings

OTHER PUBLICATIONS

Stephen M. Berge et al., Pharmaceutical Salts, Journal of Pharmaceutical Sciences, Jan. 1977, vol. 66 No. 1, pp. 1-19.
Bonhaus, D. W., RO436854, a high affinity, selective, CNS penetrating 5-HT6 receptor antagonist, Society for Neuroscience, Abstract Archive: 2000-2005, Neuroscience 2002 Abstract, Nov. 7, 2002.
Theresa A. Brancheck, 5-HT6 Receptors as Emerging Targets for Drug Discovery, Annu. Rev. Pharmacol. Toxicol. 2000, pp. 319-334.
Steven M. Bromidge, et al., 5-Chloro-N-(4-methoxy-3-piperazin-1-yl-phenyl)-3-methyl-2-benzothiophenesulfon-amide (SB-271046): A Potent, Selective, and Orally Bioavailable 5-HT6 Receptor Antagonist, J. Med. Chem. 1999, 42, pp. 202-205.
Steven M. Bromidge, et al., Phenyl Benzenesulfonamides are Novel and Selective 5-HT6 Antagonists: Identification of N-(2,5-Dibromo-3-fluorophenyl)-4-methoxy-3-piperazin-1-ylbenzenesulfonamide (SB-357134), Biorganic & Medicinal Chemistry Letters 11 (2001), pp. 55-58.
C. Reavill et al., The therapeutic potential of 5-HT6 receptor antagonists, Current Opinion in Investigational Drugs, 2001, pp. 104-109.
Callahan, P. M., Characterization of the selective 5-HT6 receptor antagonist SB 271046 in behavioral models of cognition, Society for Neuroscience, Abstract Archive: 2000-2005, Neuroscience 2004 Abstract, Oct. 26, 2004.
Frederick J. Monsma, Jr., Cloning and Expression of a Novel Serotonin Receptor with High Affinity for Tricyclic Psychotropic Drugs, The American Society for Pharmocology and Experimental Therapeutics, Molecular Pharmacology, 1992, 43;320-327.
L. A. Dawson et al, In vivo effects of the 5-HT6 antagonist SB-271046 on striatal and frontal cortex extracellular concentrations of noradrenaline, dopamine, 5-HT, glutamate and aspartate, British Journal of Pharmacology (2000) 130, 23-26.
A. Ennaceur et al, A new one-trial test for neruobiological studies of memory in rats. 1: Behavioral data, Behavioural Brain Research, 31 (1998) 47-59.
Monique Ernst et al, DOPA Decarboxylase Activity in Attention Deficit Hyperactivity Disorder Adults. A [Fluorine-18]Fluorodopa Positron Emission Tomographic Study, The Journal of Neuroscience, Aug. 1, 1998 18(15): 5901-5907.
Gerard B. Fox et al, Memory Consolidation Induces a Transient and Time-Dependent Increase in the Frequency of Neural Cell Adhesion Molecule Polysialylated Cells in the Adult Rat Hippocampus, Journal of Neurochemistry, vol. 65, No. 6, 1995 International Society for Neurochemistry, pp. 2796-2799.
Caroline Gerard et al, Immuno-localization of serotonin 5-HT6 receptor-like material in the rat central nervous system, Brain Research 746 (1997) 207-219, Elsevier.
Richard A. Glennon, 2-Substituted Tryptamines: Agents with Selectivity for 5-HT6 Serotonin Receptors, J. Med. Chem. 2000, 43, 1011-1018.
Jorg Holenz et al, Medicinal chemistry strategies to 5-HT6 receptor ligands as potential cognitive enhancers and antibesity agents, Drug Discovery Today, vol. 11, Nos. 7/8, Apr. 2006, pp. 283-299.
Ants Kask et al, Neuropeptide Y Y5 receptor antagonist CGP71683A: the effects on food intake and anxiety-related behavior in the rat, European Journal of Pharmacology 414 (2001) 215-224.
M. V. King et al, 5-HT6 receptor antagonists reverse delay-dependent deficits in novel object discrimination by enhancing consolidation—an effect sensitive to NMDA receptor antagonism, Neuropharmacology 47 (2004) 195-204.
Ruth Kohen, Cloning, Characterization, and Chromosomal Localization of a Human 5-HT6 Serotonin Receptor, Journal of Neurochemistry, vol. 66, No. 1, 1996, 1996 International Society for Neurochemistry, pp. 47-56.
Mark D. Lindner, An Assessment of the Effects of Serotonin 6 (5-HT6) Receptor Antagonists in Rodent Models of Learning, The Journal of Pharmacology and Experimental Therapeutics, vol. 307, No. 2, pp. 682-691, 2003.
Cecilia Mattsson et al, 2-Alkyl-3-(1,2,3,6-tetrahydropyridin-4-yl)-1H-indoles as novel 5-HT6 receptor agonists, Bioorganic & Medicinal Chemistry Letters 15 (2005) 4230-4234.
Derek C. Cole et al, MEDI 17, Discovery of a potent, selective and orally active 5-HT6 receptor agonist, WAY-181187, The 230th ACS National Meeting, in Washington, DC, 2005.
Frederick J. Monsma, Jr. et al, Cloning and Expression of a Novel Serotonin Receptor with High Affinity for Tricyclic Psychotropic Drugs, The American Society for Pharmacology and Experimental Therapeutics, Molecular Pharmacology, 43:320-327, 1993.
R. P. Ward et al, Localization of Serotonin Subtype 6 Receptor Messenger RNA in the rat brain by in situ Hybridization Histochemistry, Neuroscience vol. 64, No. 4, pp. 1105-111, 1995.
M.L. Woolley et al, A role for 5-HT6 receptors in retention of spatial learning in the Morris water maze, Neuropharmacology 41 (2001) pp. 210-219.
N. Yamada et al, Improvement of scopolamine-induced memory impairment by Z-ajoene in water maze in mice, Pharmacology, Biochemistry and Behavior 78 (2004) 787-791.
B. Pouzet et al, Effects of the 5-HT6 receptor antagonist, SB-271046, in animal models for schizophrenia, Pharmacology, Biochemistry and Behavior 71 (2002) 635-693.
Manik R. Pullagurla et al, Possible differences in modes of agonist and antagonist binding at human 5-HT6 receptors, Bioorganic & Medicinal Chemistry Letters 14 (2004) 4569-4573.
D.C. Rogers et al, The selective 5HT6 receptor antagonist, SB-271046-A, enhances performance of maze tasks in the rat, Neuroscience Research, SmithKline Beecham Pharmaceut, Harlow Essex CM19-5AW, United Kingdom, 2000.
Bryan L. Roth et al, Binding of Typical and Atypical Antipsychotic Agents to 5-Hydroxytryptamine-6 and 5-Hydroxytryptamine-7 receptors, The Journal of Pharmacology and Experimental and Experimental Therapeutics, vol. 268, No. 3, 1994, The American Society for Pharmacology and Experimental Therapeutics.
Carol Routledge et al, Characterization of SB-271046: A potent, selective and orally active 5-HT6 receptor antagonist, British Journal of Pharmacology (2000) 130, 1606-1612.
Martial Ruat et al, A novel rat serotonin (5-HT6) receptor: molecular cloning, localization and stimulation of cAMP accumulation, Biochemical and biophysical research communications, vol. 193, No. 1, 1993, pp. 268-276.
Andrew J. Sleight et al, Characterization of Ro 04-6790 and Ro 63-0563: potent and selective antagonists at human and rat 5-HT6 receptors, British Journal of Pharmacology (1998) 124, 556-562.
Hirst, W. D. et al, Characterization of SB-399885, a potent and selective 5-HT6 receptor antagonist, Society for Neuroscience, Abstract Archive: 2000-2005, Neuroscience 2003 Abstract, Oct. 26, 2004.
E.S.J. Robinson et al, Uptake of fluorescently labelled antisense to u 2A/D-adrenoceptors into rat brain following i.c.v. injection, Psychopharmacology Unit, University of Bristol, pp. 55P-131P (1999).
Yuching Tsai et al, N1-(Benzenesulfonyl)tryptarnines as Novel 5-HT6 Antagonists, Bioorganic & Medicinal Letters 10 (2000) 2295-2299.
Andrew V. Turnbull et al, Selective Antagonism of the NPY Y5 Receptor Does Not Have a Major Effect on Feeding in Rats, Diabetes, vol. 51, Aug. 2002, pp. 2441-2449.

* cited by examiner

1 …

ARYL SULFONAMIDE AMINE COMPOUNDS AND THEIR USE AS 5-HT6 LIGANDS

FIELD OF INVENTION

The present invention relates to novel aryl sulfonamide amine compounds of the formula (I), their tautomeric forms, their stereoisomers, their polymorphs, their pharmaceutically acceptable salts, their pharmaceutically acceptable solvates described herein and pharmaceutically acceptable compositions containing them.

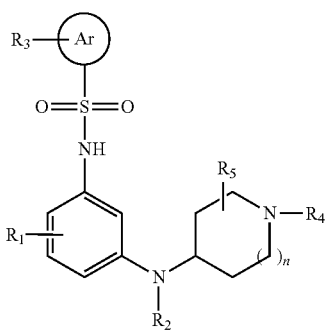

The present invention also relates to a process for the preparation of above said novel compounds, their tautomeric forms, their stereoisomers, their polymorphs, their pharmaceutically acceptable salts, their pharmaceutically acceptable solvates described herein and pharmaceutically acceptable compositions containing them.

These compounds are useful in the treatment or prevention of various disorders that are related to 5-$HT_6$ receptor functions.

BACKGROUND OF THE INVENTION

Various central nervous system disorders such as anxiety, depression, motor disorders etc., are believed to involve a disturbance of the neurotransmitter 5-hydroxytryptamine (5-HT) or serotonin. Serotonin is localized in the central and peripheral nervous systems and is known to affect many types of conditions including psychiatric disorders, motor activity, feeding behavior, sexual activity and neuroendocrine regulation among others. 5-HT receptor subtypes regulate the various effects of serotonin. Known 5-HT receptor family includes the 5-$HT_1$ family (e.g. 5-$HT_{1A}$), the 5-$HT_2$ family (e.g. 5-$HT_{2A}$ & 5-$HT_{2C}$), 5-$HT_3$, 5-$HT_4$, 5-$HT_5$, 5-$HT_6$ and 5-$HT_7$ subtypes.

The 5-$HT_6$ receptor subtype was first cloned from rat tissue in 1993 (Monsma, F. J.; Shen, Y.; Ward, R. P.; Hamblin, M. W., Sibley, D. R., Molecular Pharmacology, 1993, 43, 320-327) and subsequently from human tissue (Kohen, R.; Metcalf, M. A.; Khan, N.; Druck, T.; Huebner, K.; Sibley, D. R., Journal of Neurochemistry, 1996, 66, 47-56). The receptor is a G-protein coupled receptor (GPCR) positively coupled to adenylate cyclase (Ruat, M.; Traiffort, E.; Arrang, J-M.; Tardivel-Lacombe, L.; Diaz, L.; Leurs, R.; Schwartz, J-C., Biochemical Biophysical Research Communications, 1993, 193, 268-276). The receptor is found almost exclusively in the central nervous system (CNS) areas both in rats as well as in humans.

In situ hybridization studies of 5-$HT_6$ receptor in rat brain using mRNA indicate principal localization in the areas of 5-HT projection including striatum, nucleus accumbens, olfactory tubercle and hippocampal formation (Ward, R. P.; Hamblin, M. W.; Lachowicz, J. E.; Hoffman, B. J.; Sibley, D. R.; Dorsa, D. M., Neuroscience, 1995, 64, 1105-1111). Highest levels of 5-$HT_6$ receptor mRNA has been observed in the olfactory tubercle, the striatum, nucleus accumbens, and dentate gyrus as well as $CA_1$, $CA_2$ and $CA_3$ regions of the hippocampus. Lower levels of 5-$HT_6$ receptor mRNA were seen in the granular layer of the cerebellum, several diencephalic nuclei, amygdala and in the cortex. Northern blots have revealed that 5-$HT_6$ receptor mRNA appears to be exclusively present in the brain, with little evidence for its presence in peripheral tissues.

The high affinity of number of antipsychotic agents towards 5-$HT_6$ receptor, the localization of its mRNA in striatum, olfactory tubercle and nucleus accumbens suggests that some of the clinical actions of these compounds may be mediated through this receptor. Its ability to bind wide range of therapeutic compounds used in psychiatry, coupled with its intriguing distribution in the brain has stimulated significant interest in new compounds which are capable of interacting with the said receptor (Sleight, A. J. et al. 5-$HT_6$ and 5-$HT_7$ receptors: molecular biology, functional correlates and possible therapeutic indications, Drug News Perspective. 1997, 10, 214-224). Significant efforts are being made to understand the possible role of the 5-$HT_6$ receptor in psychiatry, cognitive dysfunction, motor function and control, memory, mood and the like. The compounds which demonstrate a binding affinity for the 5-$HT_6$ receptor are earnestly sought both as an aid in the study of the 5-$HT_6$ receptor and as potential therapeutic agents in the treatment of central nervous system disorders, for example see Reavill C. and Rogers D. C., Current Opinion in Investigational Drugs, 2001, 2(1): 104-109, Pharma Press Ltd.

Monsma F. J. et al. (1993) and Kohen, R. et al. (2001) have shown that several tricyclic antidepressant compounds, such as amitriptyline and atypical antidepressant compounds, such as mianserin have high affinity for the 5-$HT_6$ receptor. These findings have led to the hypothesis that the 5-$HT_6$ receptor is involved in the pathogenesis and/or treatment of affective disorders. Rodent models of anxiety-related behaviour yield conflicting results about the role of the 5-$HT_6$ receptor in anxiety. Treatment with 5-$HT_6$ receptor antagonists increases seizure threshold in a rat maximal electroconvulsive-shock test [Stean, T. et al. Anticonvulsant properties of the selective 5-$HT_6$ receptor antagonist SB-271046 in the rat maximal electroshock seizure threshold test. British Journal of Pharmacology, 1999, 127, Proc. Supplement-131P; Routledge, C. et al. Characterization of SB-271046: a potent, selective and orally active 5-$HT_6$ receptor antagonist. British Journal of Pharmacology, 2000, 130, 1606-1612]. Although this indicates that 5-$HT_6$ receptors might regulate seizure threshold, the effect is not as pronounced as that of known anticonvulsant drugs.

Our understanding of the roles of 5-$HT_6$ receptor ligands is most advanced in two therapeutic indications in which this receptor is likely to have a major role: learning and memory deficits and abnormal feeding behaviour. The exact role of the 5-$HT_6$ receptor is yet to be established in other CNS indications such as anxiety, although one 5-$HT_6$ agonist has reached Phase I clinical trials recently. There are many potential therapeutic uses for 5-$HT_6$ receptor ligands in humans based on direct effects and on indications from available scientific studies. These studies include the localization of the receptor, the affinity of ligands with known in-vivo activity and various animal studies conducted so far. Preferably, antagonist compounds of 5-HT$_6$ receptors are sought after as therapeutic agents.

One potential therapeutic use of modulators of 5-HT$_6$ receptor functions is in the enhancement of cognition and memory in human diseases such as Alzheimer's. The high levels of receptor found in structures such as the forebrain, including the caudate/putamen, hippocampus, nucleus accumbens and cortex suggests a role for the receptor in memory and cognition since these areas are known to play a vital role in memory (Gerard, C.; Martres, M. P.; Lefevre, K.; Miguel, M. C.; Verge, D.; Lanfumey, R.; Doucet, E.; Hamon, M.; E I Mestikawy, S., Brain Research, 1997, 746, 207-219). The ability of known 5-HT$_6$ receptor ligands to enhance cholinergic transmission also supports the potential cognition use (Bentley, J. C.; Boursson, A.; Boess, F. G.; Kone, F. C.; Marsden, C. A.; Petit, N.; Sleight, A. J., British Journal of Pharmacology, 1999, 126 (7), 1537-1542).

Studies have found that a known 5-HT$_6$ selective antagonist significantly increased glutamate and aspartate levels in the frontal cortex without elevating levels of noradrenaline, dopamine or 5-HT. This selective elevation of certain neurochemicals is noted during memory and cognition, strongly suggests a role for 5-HT$_6$ ligands in cognition (Dawson, L. A.; Nguyen, H. Q.; Li, P. British Journal of Pharmacology, 2000, 130 (1), 23-26). Animal studies of memory and learning with a known selective 5-HT$_6$ antagonist have some positive effects (Rogers, D. C.; Hatcher, P. D.; Hagan, J. J. Society of Neuroscience, Abstracts, 2000, 26, 680).

A related potential therapeutic use for 5-HT$_6$ ligands is in the treatment of attention deficit disorders (ADD, also known as Attention Deficit Hyperactivity Disorder or AMID) in children as well as adults. As 5-HT$_6$ antagonists appear to enhance the activity of the nigrostriatal dopamine pathway and ADHD has been linked to abnormalities in the caudate (Ernst, M; Zametkin, A. J.; Matochik, J. H.; Jons, P. A.; Cohen, R. M., Journal of Neuroscience, 1998, 18(15), 5901-5907), 5-HT$_6$ antagonists may attenuate attention deficit disorders.

At present, a few fully selective agonists are available. The Wyeth agonist WAY-181187 is currently in Phase I trials to target anxiety [Cole, D. C. et al. (2005) Discovery of a potent, selective and orally active 5-HT$_6$ receptor agonist, WAY-181187. 230th ACS Natl. Meet. (August 28-September 1, Washington D.C.), Abstract MEDI 17.]

International Patent Publication WO 03/066056 A1 reports that antagonism of 5-HT$_6$ receptor could promote neuronal growth within the central nervous system of a mammal. Another International. Patent Publication WO 03/065046 A2 discloses new variant of human 5-HT$_6$ receptor and proposes that 5-HT$_6$ receptor is associated with numerous other disorders.

Early studies examining the affinity of various CNS ligands with known therapeutic utility or a strong structural resemblance to known drugs suggests a role for 5-HT$_6$ ligands in the treatment of schizophrenia and depression. For example, clozapine (an effective clinical antipsychotic) has high affinity for the 5-HT$_6$ receptor subtype. Also, several clinical antidepressants have high affinity for the receptor as well and act as antagonists at this site (Branchek, T. A; Blackburn, T. P., Annual Reviews in Pharmacology and Toxicology, 2000, 40, 319-334).

Further, recent in-vivo studies in rats indicate that 5-HT$_6$ modulators may be useful in the treatment of movement disorders including epilepsy (Stean, T.; Routledge, C.; Upton, N., British Journal of Pharmacology, 1999, 127 Proc. Supplement-131P; and Routledge, C.; Bromidge, S. M.; Moss, S. F.; Price, G. W.; Hirst, W.; Newman, H.; Riley, G.; Gager, T.; Stean, T.; Upton, N.; Clarke, S. E.; Brown, A. M.; British Journal of Pharmacology, 2000, 30 (7), 1606-1612).

Taken together, the above studies strongly suggest that compounds which are 5-HT$_6$ receptor modulators, i.e., ligands, may be useful for therapeutic indications including, the treatment of diseases associated with a deficit in memory, cognition and learning such as Alzheimer's and attention deficit disorder; the treatment of personality disorders such as schizophrenia; the treatment of behavioral disorders, e.g. anxiety, depression and obsessive compulsive disorders; the treatment of motion or motor disorders such as Parkinson's disease and epilepsy; the treatment of diseases associated with neurodegeneration such as stroke or head trauma; or withdrawal from drug addiction including addiction to nicotine, alcohol and other substances of abuse.

Such compounds are also expected to be of use in the treatment of certain gastrointestinal (GI) disorders such as functional bowel disorder. See for example, Roth, B. L.; et al., Journal of Pharmacology and Experimental Therapeutics, 1994, 268, 1403-1412; Sibley, D. R.; et al., Molecular Pharmacology, 1993, 43, 320-327, Sleight, A. J.; et al., Neurotransmission, 1995, 11, 1-5; and Sleight, A. J.; et al., Serotonin ID Research Alert, 1997, 2(3), 115-118.

Furthermore, the effect of 5-HT$_6$ antagonist and 5-HT$_6$ antisense oligonucleotides to reduce food intake in rats has been reported, thus potentially in treatment of obesity. See for example, Bentley, J. C.; Boursson, A.; Boess, F. G.; Kone, F. C.; Marsden, C. A.; Petit, N.; Sleight, A. J., British Journal of Pharmacology, 1999, 126 (7), 1537-1542); Wooley et al., Neuropharmacology, 2001, 41: 210-129 and WO 02/098878.

A recent review by Holenz, Jo''rg et. al., Drug Discovery Today, 11, 7/8, April 2006, Medicinal chemistry strategies to 5-HT$_6$ receptor ligands as potential cognitive enhancers and antiobesity agents, gives elaborate discussion on evolution of 5-HT$_6$ ligands. It had summarized pharmacological tools and preclinical candidates used in evaluation of 5-HT$_6$ receptor in illnesses such as schizophrenia, other dopamine-related disorders and depression and to profile the neurochemical and electrophysiological effects of either blockade or activation of 5-HT$_6$ receptors. Recently, a review by Heal D. J. et. al. Pharmacology and therapeutics, 2008; 117, 207-231, Selective 5-HT$_6$ receptor ligands: Progress in the development of a novel pharmacological approach to the treatment of the obesity and related metabolic disorders, described the major developments in the fields of medicinal chemistry and pharmacology of 5-HT$_6$ ligands, with particular emphasis on their potential application as novel anti-obesity drugs. Furthermore, they have been used to characterize the 5-HT$_6$ receptor and to investigate its distribution.

Phase II antagonist candidate from GlaxoSmithKline, SB-742457 for the therapeutic indication of cognitive dysfunction associated with Alzheimer's disease [Ahmed, M. et al. (2003) Novel compounds. WO patent 2003080580] and the Lilly compound LY-483518 [Filla, S. A. et al. (2002) Preparation of benzenesulfonic acid indol-5-yl esters as antagonists of the 5-HT$_6$ receptor, WO 2002060871] has been reported. SB-271046, the first 5-HT$_6$ receptor antagonist to enter Phase I clinical development, has been discontinued (probably because of low penetration of the blood-brain barrier). In addition, the selective 5-HT$_6$ receptor antagonist SB-271046 is inactive in animal tests related to either positive or negative symptoms of schizophrenia [Pouzet, B. et al. Effects of the 5-HT$_6$ receptor antagonist, SB-271046, in animal models for schizophrenia. Pharmacol. Biochem. Behay. 2002, 71, 635-643].

International Patent Publications WO 2007/046112, WO 2007/020653, WO2007/138611, WO 2005/066157, WO 2004/108671, WO 2004/048331, WO 2004/048330 and WO 2004/048328 (all assigned to Suven Life Sciences Limited) describe the related prior art. Further WO 98/27081, WO 99/02502, WO 99/37623, WO 99/42465 and WO 01/32646 (all assigned to Glaxo SmithKline Beecham PLC) disclose a series of aryl sulfonamide and sulfoxide compounds as 5-HT$_6$ receptor antagonists and are claimed to be useful in the treatment of various CNS disorders. While some 5-HT$_6$ modulators have been disclosed, there continues to be a need for compounds that are useful for modulating 5-HT$_6$. In our research in area of 5-HT$_6$ receptors, we found that aryl sulfonamide amine compounds of formula (I) demonstrate very high 5-HT$_6$ receptor affinity. Therefore, it is an object of this invention to provide compounds, which are useful as therapeutic agents in the treatment/prevention of a variety of central nervous system disorders or disorders affected by the 5-HT$_6$ receptor.

SUMMARY OF THE INVENTION

The present invention relates to novel aryl sulfonamide amine compounds of the formula (I), their tautomeric forms, their stereoisomers, their polymorphs, their pharmaceutically acceptable salts, their pharmaceutically acceptable solvates described herein and pharmaceutically acceptable compositions containing them.

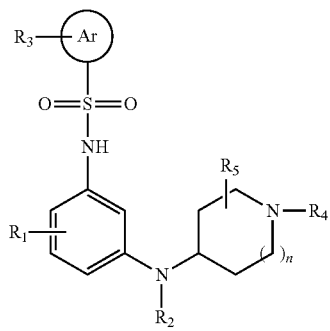

(I)

wherein $R_1$, $R_2$, $R_3$ and $R_5$ may be same or different and each independently represent hydrogen, halogen, $(C_1-C_3)$alkyl, $(C_1-C_3)$alkoxy, cyclo$(C_3-C_6)$alkyl, cyclo$(C_3-C_6)$alkoxy, halo$(C_1-C_3)$alkyl or halo$(C_1-C_3)$alkoxy;

represents aryl or heterocycle;

$R_4$ represents hydrogen, $(C_1-C_3)$alkyl, cyclo$(C_3-C_6)$alkyl, halo$(C_1-C_3)$alkyl, aryl or aralkyl;

"n" represents 1 to 2;

The present invention relates to use of a therapeutically effective amount of compound of formula (I), to manufacture a medicament in the treatment/prevention of various disorders that are related to 5-HT$_6$ receptor functions.

Specifically, the compounds of this invention are useful in the treatment of various disorders such as anxiety, Alzheimer's disease, depression, convulsive disorders, obsessive-compulsive disorders, migraine, headache, cognitive memory disorders, ADHD (Attention Deficient Disorder/Hyperactivity Syndrome), personality disorders, psychosis, paraphrenia, psychotic depression, Parkinson's disease, mania, schizophrenia, panic disorders, sleep disorders, withdrawal from drug abuse syndrome, stroke, head trauma, mild cognitive impairment, neurodegenerative disorders, gastrointestinal and obesity.

In another aspect, the invention relates to pharmaceutical compositions containing a therapeutically effective amount of at least one compound of formula (I) or individual stereoisomers, racemic or non-racemic mixture of stereoisomers or pharmaceutically acceptable salts or solvates thereof, in admixture with at least one suitable carrier, diluents, adjuvants or excipients.

In another aspect, the invention relates to a radiolabeled compound of formula (I) for use in medical diagnosis or therapy, as well as the use of a radiolabeled compound of formula (I) to prepare a medicament useful in the treatment of various disorders that are related to 5-HT$_6$ receptor functions.

In another aspect, the invention relates to the use of a compound according to the present invention in combination with at least one further active ingredient for manufacture of a medicament for the treatment or prevention of diseases and conditions.

In still another aspect, the invention further relates to compositions comprising and methods for using compounds of formula (I).

In yet another aspect, the invention further relates to the process for preparing compounds of formula (I).

Following is the partial list of the compounds belonging to general formula (I):

N-[4-Chloro-3-(1-methylpiperidin-4-ylamino)phenyl]benzenesulfonamide;
4-Fluoro-N-[4-Chloro-3-(1-methylpiperidin-4-ylamino) phenyl]benzenesulfonamide;
4-Methyl-N-[4-Chloro-3-(1-methylpiperidin-4-ylamino) phenyl]benzenesulfonamide;
4-Isopropyl-N-[4-Chloro-3-(1-methylpiperidin-4-ylamino) phenyl]benzenesulfonamide;
2-Bromo-N-[4-Chloro-3-(1-methylpiperidin-4-ylamino) phenyl]benzenesulfonamide;
4-Fluoro-N-[4-Methoxy-3-(1-methylpiperidin-4-ylamino) phenyl]benzenesulfonamide;
N-[4-Methoxy-3-(1-methylpiperidin-4-ylamino)phenyl] benzenesulfonamide;
2-Bromo-N-[4-Methoxy-3-(1-methylpiperidin-4-ylamino) phenyl]benzenesulfonamide;
4-Isopropyl-N-[4-Methoxy-3-(1-methylpiperidin-4-ylamino)phenyl]benzenesulfonamide;
4-Methyl-N-[4-Methoxy-3-(1-methylpiperidin-4-ylamino) phenyl]benzenesulfonamide;
2-Bromo-N-[3-(1-methylpiperidin-4-ylamino)phenyl]benzenesulfonamide;
4-Isopropyl-N-[3-(1-methylpiperidin-4-ylamino)phenyl] benzenesulfonamide;
4-Fluoro-N-[3-(1-methylpiperidin-4-ylamino)phenyl]benzenesulfonamide;
4-Methyl-N-[3-(1-methylpiperidin-4-ylamino)phenyl]benzenesulfonamide;
2-Bromo-N-[4-Methyl-3-(1-methylpiperidin-4-ylamino) phenyl]benzenesulfonamide;
N-[4-Methyl-3-(1-methylpiperidin-4-ylamino)phenyl]benzenesulfonamide;
4-Fluoro-N-[4-Methyl-3-(1-Methylpiperidin-4-ylamino) phenyl]benzenesulfonamide;
4-Methyl-N-[4-Methyl-3-(1-Methylpiperidin-4-ylamino) phenyl]benzenesulfonamide;

N-[3-(1-methylpiperidin-4-ylamino)phenyl]benzenesulfonamide;

5-Chloro-3-methyl-N-[4-methoxy-3-(1-methylpiperidin-4-ylamino)phenyl]benzo[b]thiophene-2-yl sulfonamide;

N-[4-Chloro-3-(1-methylpiperidin-4-ylamino)phenyl]benzenesulfonamide hydrochloride;

4-Isopropyl-N-[4-Methyl-3-(1-Methylpiperidin-4-ylamino)phenyl]benzenesulfonamide hydrochloride;

2-Bromo-N-{4-methoxy-3-[N-methyl-N-(1-methyl piperidin-4-yl)amino]phenyl}benzenesulfonamide;

N-[4-Bromo-3-(1-methylpiperidin-4-ylamino)phenyl]benzenesulfonamide;

N-[4-Ethoxy-3-(1-methylpiperidin-4-ylamino)phenyl]benzenesulfonamide;

N-[4-Trifluoromethyl-3-(piperidin-4-ylamino)phenyl]benzenesulfonamide;

4-Fluoro-N-[4-fluoro-3-(1-methylpiperidin-4-ylamino)phenyl]benzenesulfonamide;

4-Fluoro-N-[4-Methoxy-3-(piperidin-1-ylamino) phenyl] benzenesulfonamide;

4-Methyl-N-[4-bromo-3-(1-methylpiperidin-4-ylamino)phenyl]benzenesulfonamide;

4-Methyl-N-[4-ethoxy-3-(piperidin-1-ylamino)phenyl]benzenesulfonamide;

4-Isopropyl-N-[4-trifluoromethoxy-3-(1-methylpiperidin-4-ylamino)phenyl]benzenesulfonamide;

4-Isopropyl N-[4-Chloro-3-(piperidin-1-ylamino)phenyl] benzenesulfonamide;

2-Bromo-N-[4-Chloro-3-(piperidin-1-ylamino)phenyl]benzenesulfonamide;

4-Bromo-N-[3-(1-methylpiperidin-4-ylamino)phenyl]benzenesulfonamide;

4-Bromo-N-[4-chloro-3-(1-methylpiperidin-4-ylamino)phenyl]benzenesulfonamide;

4-Methoxy-N-[4-bromo-3-(1-methylpiperidin-4-ylamino)phenyl]benzenesulfonamide;

4-Methoxy-N-[4-trifluoromethyl-3-(piperidin-1-ylamino)phenyl]benzenesulfonamide;

2,4-Dichloro-N-[4-methoxy-3-(1-methylpiperidin-4-ylamino)phenyl]benzenesulfonamide;

2,4-Dichloro-N-[4-bromo-3-(piperidin-1-ylamino)phenyl]benzenesulfonamide;

4-Trifluoromethoxy-N-[4-chloro-3-(1-methylpiperidin-4-ylamino)phenyl]benzenesulfonamide;

4-chloro-N-[4-Chloro-3-(piperidin-1-ylamino)phenyl]benzenesulfonamide;

2-Chloro-N-[4-chloro-3-(1-methylpiperidin-4-ylamino)phenyl]benzenesulfonamide;

2-Methoxy-N-[4-trifluoromethyl-3-(piperidin-1-ylamino) phenyl]benzenesulfonamide;

4-Methyl-N-[4-Chloro-3-[N-methyl-N-(4-methylpiperidin-1-yl)amino]phenyl]benzenesulfonamide;

4-Methyl-N-[4-Methoxy-3-[N-methyl-N-(4-methylpiperidin-1-yl)amino]phenyl]benzenesulfonamide;

4-Methyl-N-[4-fluoro-3-[N-methyl-N-(piperidin-1-yl)amino]phenyl]benzenesulfonamide and 4-Methyl-N-[4-trifluoromethyl-3-[N-methyl-N-(piperidin-1-yl)amino]phenyl]benzenesulfonamide;

and its tautomeric forms, its stereoisomers, its polymorphs, its pharmaceutically acceptable salts and solvates.

DETAILED DESCRIPTION OF THE INVENTION

Unless otherwise stated, the following terms used in the specification and claims have the meanings given below:

"Halogen" means fluorine, chlorine, bromine or iodine;

"$(C_1-C_3)$alkyl" means straight or branched chain alkyl radicals containing one to three carbon atoms and includes methyl, ethyl, n-propyl or iso-propyl;

"$(C_1-C_3)$alkoxy" means straight or branched chain alkyl radicals containing one to three carbon atoms and includes methoxy, ethoxy, propyloxy or iso-propyloxy;

"Cyclo$(C_3-C_6)$alkyl" means cyclic or branched cyclic alkyl radicals containing three to six carbon atoms and includes cyclopropyl, cyclobutyl, cyclopentyl, cyclopropylmethyl, cyclo$(C_3-C_6)$alkyl methyl or cyclohexyl, which may be substituted or unsubstituted and optionally the substituents may be selected from halogen, $(C_1-C_3)$alkyl or $(C_1-C_3)$alkoxy;

"Cyclo$(C_3-C_6)$alkoxy" means cyclic and branched cyclic alkyl radicals containing from three to six carbon atoms and includes cyclopropyloxy, cyclobutyloxy, cyclopentyloxy or cyclohexyloxy;

"Halo$(C_1-C_3)$alkyl" means straight or branched chain alkyl radicals containing one to three carbon atoms and includes' fluoromethyl, difluoromethyl, trifluoromethyl, trifluoroethyl, fluoroethyl, difluoroethyl and the like;

"Halo$(C_1-C_3)$alkoxy" means straight or branched chain alkyl radicals containing one to three carbon atoms and includes fluoromethoxy, difluoromethoxy, trifluoromethoxy, trifluoroethoxy, fluoroethoxy, difluoroethoxy and the like;

"Heterocycle" means organic compounds that contain a ring structure containing atoms in addition to carbon such as sulfur, oxygen or nitrogen, as part of the ring. They may be either simple aromatic rings or non-aromatic rings and includes pyridine, pyrimidine, benzothiophene and the like;

"Aryl" means monocyclic aromatic ring system, which can optionally be substituted with hydrogen, halogen, $(C_1-C_3)$ alkyl, halo$(C_1-C_3)$alkyl, $(C_1-C_3)$alkoxy or halo $(C_1-C_3)$ alkoxy;

"Aralkyl" means benzyl or heterocyclylmethyl and the like;

The term "schizophrenia" means schizophrenia, schizophreniform and schizoaffective disorder.

The term "psychotic disorder" refers to delusions, prominent hallucinations, disorganized speech or disorganized or catatonic behavior. See Diagnostic and Statistical Manual of Mental Disorder; fourth edition, American Psychiatric Association, Washington, D.C.

The phrase "pharmaceutically acceptable salts" indicates that the substance or composition must be compatible chemically and/or toxicologically, with the other ingredients comprising a formulation, the mammal being treated therewith.

"Therapeutically effective amount" is defined as 'an amount of a compound of the present invention that (i) treats or prevents the particular disease, condition or disorder (ii) attenuates, ameliorates or eliminates one or more symptoms of the particular disease, condition or disorder (iii) prevents or delays the onset of one or more symptoms of the particular disease, condition or disorder described herein'.

The terms "treating", "treat" or "treatment" embrace all the meanings such as preventative, prophylactic and palliative.

The term "stereoisomers" is a general term for all isomers of the individual molecules that differ only in the orientation of their atoms in space. It includes mirror image isomers (enantiomers), geometric (cis-trans) isomers and isomers of compounds with more than one chiral centre that are not mirror images of one another (diastereomers).

The term "ADHD" means Attention Deficit Hyperactivity Disorder.

Certain compounds of formula (I) are capable of existing in stereoisomeric forms (e.g. diastereomers and enantiomers) and the invention extends to each of these stereoisomeric forms and to mixtures thereof including racemates. The different stereoisomeric forms may be separated from one another by the usual methods or any given isomer may be obtained by stereospecific or asymmetric synthesis. The invention also extends to tautomeric forms and mixtures thereof.

The stereoisomers as a rule are generally obtained as racemates that can be separated into the optically active isomers in a manner known per se. In the case of the compounds of general formula (I) having an asymmetric carbon atom the present invention relates to the D-form, the L-form and D,L-mixtures and in the case of a number of asymmetric carbon atoms, the diastereomeric forms and the invention extends to each of these stereo isomeric forms and to mixtures thereof including racemates. Those compounds of general formula (I) which have an asymmetric carbon and as a rule are obtained as racemates can be separated one from the other by the usual methods, or any given isomer may be obtained by stereo specific or asymmetric synthesis. However, it is also possible to employ an optically active compound from the start, a correspondingly optically active enantiomeric or diastereomeric compound then being obtained as the final compound.

The stereoisomers of compounds of general formula (I) may be prepared by one or more ways presented below:
i) One or more of the reagents may be used in their optically active form.
ii) Optically pure catalyst or chiral ligands along with metal catalyst may be employed in the reduction process. The metal catalyst may be Rhodium, Ruthenium, Indium and the like. The chiral ligands may preferably be chiral phosphines (Principles of Asymmetric synthesis, J. E. Baldwin Ed., Tetrahedron series, 14, 311-316).
iii) The mixture of stereoisomers may be resolved by conventional methods such as forming diastereomeric salts with chiral acids or chiral amines or chiral amino alcohols, chiral amino acids. The resulting mixture of diastereomers may then be separated by methods such as fractional crystallization, chromatography and the like, which is followed by an additional step of isolating the optically active product by hydrolyzing the derivative (Jacques et. al., "Enantiomers, Racemates and Resolution", Wiley Interscience, 1981).
iv) The mixture of stereoisomers may be resolved by conventional methods such as microbial resolution, resolving the diastereomeric salts formed with chiral acids or chiral bases.

Chiral acids that can be employed may be tartaric acid, mandelic acid, lactic acid, camphorsulfonic acid, amino acids and the like. Chiral bases that can be employed may be cinchona alkaloids, brucine or a basic amino acid such as lysine, arginine and the like. In the case of the compounds of general formula (I) containing geometric isomerism the present invention relates to all of these geometric isomers.

Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid and organic acids e.g. succinic, maleic, acetic, fumaric, citric, tartaric, benzoic, p-toluenesulfonic, methanesulfonic or naphthalenesulfonic acid. The present invention includes, within its scope, all possible stoichiometric and non-stoichiometric forms.

The pharmaceutically acceptable salts forming a part of this invention may be prepared by treating the compound of formula (I) with 1-6 equivalents of a base such as sodium hydride, sodium methoxide, sodium ethoxide, sodium hydroxide, potassium t-butoxide, calcium hydroxide, calcium acetate, calcium chloride, magnesium hydroxide, magnesium chloride and the like. Solvents such as water, acetone, ether, THF, methanol, ethanol, t-butanol, dioxane, isopropanol, isopropyl ether or mixtures thereof may be used.

The compounds of formula (I) may be prepared in crystalline or non-crystalline form and if crystalline, may optionally be solvated, eg. as the hydrate. This invention includes within its scope stoichiometric solvates (eg. hydrates) as well as compounds containing variable amounts of solvent (eg. water).

The compounds of the invention can be used in combination, with each other or with other therapeutic agents or approaches used to treat or prevent the conditions listed above. Such agents or approaches include beta-secretase inhibitors; gamma-secretase inhibitors; amyloid aggregation inhibitors (e.g. ALZHEMED, commonly known as 3-APS, homotaurine, or Tramiprosate); directly or indirectly acting neuroprotective compounds; anti-oxidants such as Vitamin E and ginkgolide; anti inflammatory agents such as Cox-inhibitors or NSAID's; 3-hydroxy-3-glutary-CoA (HMG-CoA) Reductase Inhibitors (statins); acetylcholine-esterase inhibitors such as donepezil, rivastigmine, tacrine, galantamine; N-methyl-D-aspartate (NMDA) receptor antagonists (e.g. memantine); α-amino-3-hydroxy-5-methyl-4-isoxazolepropionic acid (AMPA) agonists; compounds which modulate the release or concentration of neurotransmitters (e.g. NS-2330); compounds inducing the release of growth hormones (e.g. ibutamoren mesylate and capromorelin); cannabinoid CB1 receptor antagonists or inverse agonists; antibiotic like minocyclin or rifampicin; phosphodiesterase-IV (PDE-IV) and phosphodiesterase-IX (PDE-IX) inhibitors; γ-aminobutyric $acid_A$ ($GABA_A$) inverse agonists; nicotinic agonists: histamine H3 antagonists, 5-hydroxytryptamine$_4$ (5-HT$_4$) agonists or partial agonists; 5-hydroxytryptamine$_6$ (5-HT$_6$) antagonists; a2-adrenoreceptor antagonists; muscarinic M1 agonists; muscarinic M2 antagonists; metabotrophic glutamaic-receptor 5 positive modulators; and compounds, which modulate receptors, oder enzymes in such a way, that the efficacy and/or safety of the compounds of the present invention is increased or side effects are reduced.

Preferred are such combinations comprising one or more of the compounds of the present invention and one or more additional active ingredient selected from the group consisting 3-APS, vitamin E, ginkgolide, donepezil, rivastigmine, tacrine, galantamine, memantine, NS-2330, ibutamoren mesylate, capromorelin, minocycline and rifampicin.

In the combination of the present invention, the compounds of the present invention and the above mentioned combination partners may be administered separately (e.g. kit of parts) or together in one pharmaceutical composition (e.g. capsule or tablet). In addition, the administration of one element of the combination of the present invention may be prior to, concurrent to, or subsequent to the administration of the other element of the combination of the present invention may be prior to, concurrent to, or subsequent to the administration of the other element of the combination. If the compounds of the present invention and the one or more additional active ingredient are present in separate formulations these separate formulations may be administered simultaneously or sequentially.

For the treatment or prevention of the above mentioned diseases and conditions compounds of the invention can be used in combination with immunological approaches, such as, for example, immunization with A beta peptide or derivatives thereof or administration of anti-A beta peptide antibodies.

Therefore, the invention relates to the use of a compound according to the present invention in combination with at least one further active ingredient for the manufacture of a medicament for the treatment or prevention of diseases and conditions.

Numerous radioisotopes are readily available including isotopes of hydrogen, carbon, nitrogen, oxygen, phosphorus, sulfur, iodine, fluorine, bromine & chlorine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{123}$I, $^{124}$I, $^{125}$I, $^{131}$I, $^{18}$F, $^{75}$Br, $^{76}$Br, $^{77}$Br, $^{82}$Br & $^{36}$Cl.

A compound of general formula (I) can be radiolabeled by using standard techniques known in organic chemistry. Alternatively, compound of formula (I) radiolabeled with radioisotope as a substituent in one of the starting materials or in an intermediate used in the synthesis of the compound of formula (I). For example, see Arthur Murry III, D. Lloyd Williams; Organic Synthesis with Isotopes, vol. I and II, Interscience Publishers Inc., N.Y. (1958) and Melvin Calvin et al. Isotopic Carbon John Wiley and Sons Inc., N.Y. (1949).

Synthesis of radiolabeled compounds may be conveniently performed by a radioisotope supplier specializing in custom synthesis of radiolabeled probe compounds, such as Amersham Corporation, Arlington Heights, Ill.; Cambrige Isotopes Laboratories, Inc. Andover, Mass.; Wizard Laboratories, West Sacramento, Calif.; ChemSyn Laboratories, Lexena, Kans.; American Radiolabeled Chemicals, Inc. & St. Louis, Mo.;

Radiolabeled analogues of compound of formula (I) may be used in clinical studies to evaluate the role of 5-HT$_6$ receptor ligands in a variety of diseases areas, where 5-HT$_6$ receptor ligands are believed to be involved.

Radiolabeled compounds of formula (I) are useful as imaging agents and biomarker for medical therapy and diagnosis. Such radiolabeled compounds are also useful as pharmacological tools for studying 5-HT$_6$ functions and activity. For example, isotopically labeled compounds are particularly useful in SPECT (single photon emission compound tomography) and in PET (positron emission tomography).

The present invention also provides a process for the preparation of a compound of general formula (I) or a pharmaceutically acceptable salt thereof, which comprises of the following route (Scheme-I), Scheme-I

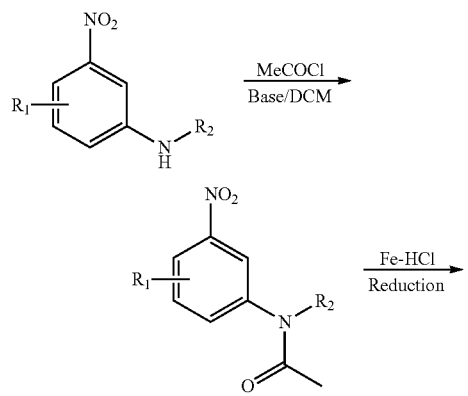

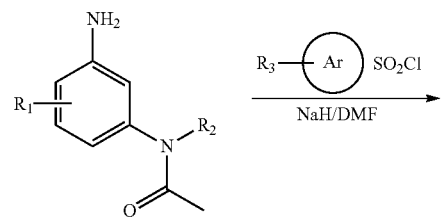

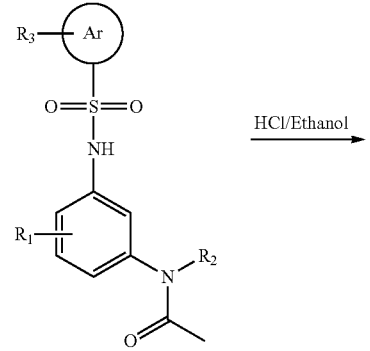

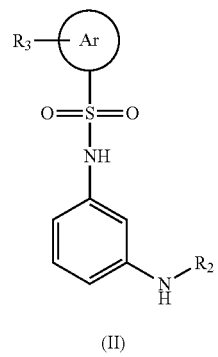

(II)

wherein the key intermediate (II) is synthesized by various methods known in literature The process of this invention includes, reacting a compound of formula (II),

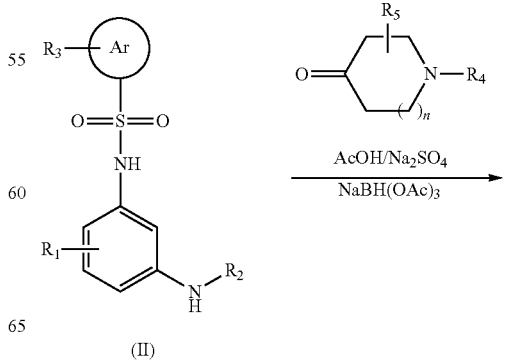

(II)

(I)

with piperidine-4-one derivatives, using a suitable reducing agent and base in presence of suitable solvent at ambient temperature to obtain a compound of formula (I), wherein all substitutions are described as earlier.

The above reaction is preferably carried out in a solvent such as ethanol, tetrahydrofuran, toluene, ethyl acetate, water, titanium isopropoxide, dimethylformamide, dimethyl sulfoxide, dimethyl ether and the like or a mixture thereof and preferably using ethyl acetate. The reaction is carried by using reducing agents like sodium, sodium borohydride, sodium cyanoborohydride, sodium triacetoxyborohydride and the like or a mixture thereof and preferably using sodium triacetoxyborohydride. The reaction may be affected in the presence of a base such as potassium carbonate, sodium hydroxide, sodium bicarbonate, sodium hydride or mixtures thereof and preferably using sodium hydroxide. The reaction temperature may range from 20° C. to 45° C. based on the choice of solvent and preferably at a temperature in the range from 20° C. to 30° C. The duration of the reaction may range from 1 to 5 hours, preferably from a period of 2 to 4 hours.

The key intermediate (II) is synthesized as described in preparation 1. This key intermediate (II) may be commercially available or they may be prepared by conventional methods or by modification, using known process.

The present invention also provides an alternate process for the preparation of a compound of general formula (I) or a pharmaceutically acceptable salt thereof, which comprises of the following route (Scheme-II), wherein the key intermediate (III) is synthesized by various methods known in literature.

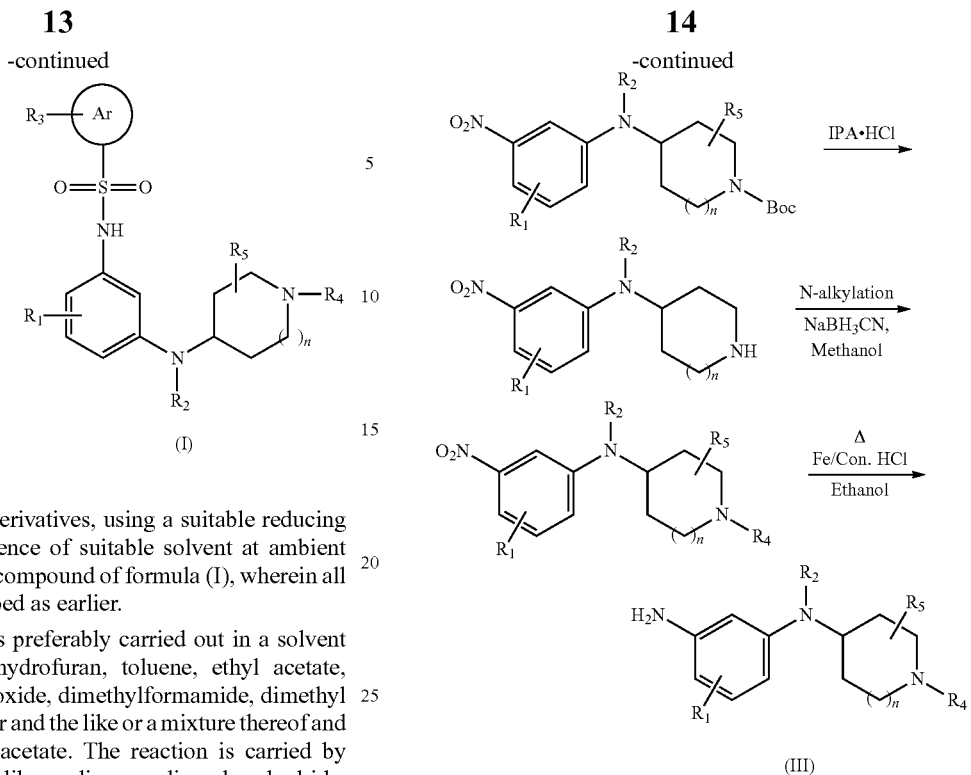

(III)

The process of this invention includes, reacting a compound of formula (III), with aryl sulfonyl chloride derivatives, in presence of suitable solvent at ambient temperature to obtain a compound of formula (I), wherein all substitutions are described as earlier.

The above reaction is preferably carried out in a solvent such as ethanol, tetrahydrofuran, toluene, ethyl acetate, water, pyridine, dichloromethane, dimethyl sulfoxide, dimethyl ether and the like or a mixture thereof and preferably using pyridine and dichloromethane. The reaction temperature may range from 20° C. to 45° C. based on the choice of solvent and preferably at a temperature in the range from 25° C. to 30° C. The duration of the reaction may range from 1 to 5 hours, preferably for period of 4 hours.

The key intermediate (III) is synthesized as described in preparation 2. This key intermediate (III) may be commercially available or they may be prepared by conventional methods or by modifications, using known process.

Compounds obtained by the above method of preparation of the present invention can be transformed into another compound of this invention by further chemical modifications using well-known reactions such as oxidation, reduction, protection, deprotection, rearrangement reaction, halogenation, hydroxylation, alkylation, alkylthiolation, demethylation, O-alkylation, O-acylation, N-alkylation, N-alkenylation, N-acylation, N-cyanation, N-sulfonylation, coupling reaction using transition metals and the like.

If necessary, any one or more than one of the following steps can be carried out, i) Converting a compound of the formula (I) into another compound of the formula (I)

ii) Removing any protecting groups; or iii) Forming a pharmaceutically acceptable salt, solvate or a prodrug thereof.

Process (i) may be performed using conventional interconversion procedures such as epimerisation, oxidation, reduction, alkylation, nucleophilic or electrophilic aromatic substitution and ester hydrolysis or amide bond formation.

In process (ii) examples of protecting groups and the means for their removal can be found in T. W. Greene Protective Groups in Organic Synthesis' (J. Wiley and Sons, 1991). Suitable amine protecting groups include sulfonyl (e.g. tosyl), acyl (e.g. acetyl, 2',2',2'-trichloroethoxycarbonyl, benzyloxycarbonyl or t-butoxycarbonyl) and arylalkyl (eg. benzyl), which may be removed by hydrolysis (e.g. using an acid such as hydrochloric or trifluoroacetic acid) or reductively (e.g. hydrogenolysis of a benzyl group or reductive removal of a 2',2',2'-trichloroethoxycarbonyl group using zinc in acetic acid) as appropriate. Other suitable amine protecting groups include trifluoroacetyl, which may be removed by base catalyzed hydrolysis or a solid phase resin bound benzyl group, such as a Merrifield resin bound 2,6-dimethoxybenzyl group (Ellman linker), which may be removed by acid catalyzed hydrolysis, for example with trifluoroacetic acid.

In process (iii) halogenation, hydroxylation, alkylation and/or pharmaceutically acceptable salts may be prepared conventionally by reaction with the appropriate acid or acid derivative as described earlier in detail.

In order to use the compounds of formula (I) in therapy, they will normally be formulated into a pharmaceutical composition in accordance with standard pharmaceutical practice.

The pharmaceutical compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or a form suitable for administration by inhalation or insufflations.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol) and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of an aerosol spray from a pressurized container or a nebulizer or from a capsule using a inhaler or insufflators. In the case of a pressurized aerosol, a suitable propellant, e.g., dichlorodifluoromethane, trichlorofluoromethane, dichlorotetrafluoroethane, carbon dioxide or other suitable gas and the dosage unit may be determined by providing a valve to deliver a metered amount. The medicament for pressurized container or nebulizer may contain a solution or suspension of the active compound while for a capsule; it preferably should be in the form of powder. Capsules and cartridges (made, for example, from gelatin) for use in an inhaler or insufflator may be formulated containing a powder mix of a compound of the invention and a suitable powder base such as lactose or starch.

Aerosol formulations for treatment of the conditions referred to above (e.g., migraine) in the average adult human are preferably arranged so that each metered dose or "puff" of aerosol contains 20 μg to 1000 μg of the compound of the invention. The overall daily dose with an aerosol will be within the range 100 μg to 10 mg. Administration may be several times daily, for example 2, 3, 4 or 8 times, giving for example, 1, 2 or 3 doses each time.

An effective amount of a compound of general formula (I) or their derivatives as defined above can be used to produce a medicament, along with conventional pharmaceutical auxiliaries, carriers and additives.

Such therapy includes multiple choices: for example, administering two compatible compounds simultaneously in a single dose form or administering each compound individually in a separate dosage; or if required at same time interval or separately in order to maximize the beneficial effect or minimize the potential side-effects of the drugs according to the known principles of pharmacology.

The dose of the active compounds can vary depending on factors such as the route of administration, age and weight of patient, nature and severity of the disease to be treated and similar factors. Therefore, any reference herein to a pharmacologically effective amount of the compounds of general formula (I) refers to the aforementioned factors. A proposed dose of the active compounds of this invention, for either oral, parenteral, nasal or buccal administration, to an average adult human, for the treatment of the conditions referred to above, is 0.1 to 200 mg of the active ingredient per unit dose which could be administered, for example, 1 to 4 times per day.

Commercial reagents were utilized without further purification. Room temperature refers to 25-30° C. IR were taken using KBr and in solid state. Unless otherwise stated, all mass spectra were carried out using ESI conditions. $^1$H-NMR spectra were recorded at 400 MHz on a Bruker instrument. Deuterated chloroform (99.8% D) was used as solvent. TMS was used as internal reference standard. Chemical shift values are expressed in parts per million (δ) values. The following abbreviations are used for the multiplicity for the NMR signals: s=singlet, bs=broad singlet, d=doublet, t=triplet, q=quartet, qui=quintet, h=heptet, dd=double doublet, dt=double triplet, tt=triplet of triplets, m=multiplet. Chromatography refers to column chromatography performed using 100-200 mesh silica gel and executed under nitrogen pressure (flash chromatography) conditions.

EXAMPLES

The novel compounds of the present invention were prepared according to the following procedures, using appropriate materials and are further exemplified by the following specific examples. The most preferred compounds of the invention are any or all of those specifically set forth in these examples. These compounds are not, however, to be construed as forming the only genus that is considered as the invention and any combination of the compounds or their moieties may itself form a genus. The following examples further illustrate details for the preparation of the compounds of the present invention. Those skilled in the art will readily understand that known variations of the conditions and process of the following preparative procedures can be used to prepare these compounds.

Preparation 1: Preparation of N-(4-chloro-3-amino phenyl)benzenesulfonamide

Step (I): Preparation of 2-chloro-5-nitro acetanilide

Placed 2-chloro-5-nitroaniline (12 grams, 70 mmol) in a 500 mL three neck round bottomed flask containing dichloromethane (110 mL) under stirring. Then add triethylamine (14.9 mL, 105 mmol) to the reaction mass drop-wise in 15 minutes at room temperature. Cooled the reaction mass to 0° C. under stirring and added acetyl chloride (6.8 mL, 84 mmol) at 0° C. over a period of 10 minutes. The reaction mass was further stirred at 20-25° C. for 3 hours. Quenched the reaction mass into 150 mL of water and extracted the product with excess of dichloromethane. The combined organic layers were washed with saturated brine solution (2×25 mL), dried over anhydrous sodium sulfate, and filtered free of salts and concentrated under vacuum to obtain oily mass (7.8 gm).

IR spectra (cm$^{-1}$): 1550, 1335, 1190;
$^1$H-NMR (δ ppm): 2.15 (3H, s), 7.51-7.53 (1H, d, J=8.56 Hz), 7.85-7.87 (1H, dd, J=2.48, 8.56 Hz), 8.21 (1H, d, J=2.46 Hz);
Mass (m/z): 215.6 (M+H)$^+$.

Step (II): Preparation of 2-chloro-5-amino acetanilide

To a 500 mL three neck round bottomed flask added 2-chloro-5-nitro acetanilide (34.0 grams, 158.5 mmol) obtained at step (I) and methanol (100 mL). The mass was stirred to obtain clear solution and then added raney nickel (3.4 grams) slowly and cautiously using methanol (20 mL). Hydrazine hydrate (39.6 mL, 792.5 mmol) was added drop-wise, under nitrogen atmosphere by maintaining mass temperature at 25-30° C. The reaction was exothermic during addition. Further stirred the reaction mass at 25-30° C. for 2 hours. Filtered the reaction mass through hyflow supercel bed and washed with methanol (50 mL). The filtrate was concentrated to obtain oily mass. Added water (200 mL) and adjusted pH to 10, by using 40% aqueous sodium hydroxide solution. The product was extracted with ethyl acetate (3×100 mL). The combined organic layers were washed with saturated brine solution (2×25 mL), dried over anhydrous sodium sulfate, filtered free of salts and concentrated under vacuum to obtain oily product (18.48 grams).

IR spectra (cm$^{-1}$): 3310, 1535, 1331, 1153;
$^1$H-NMR (δ ppm): 2.15 (3H, s), 3.68 (2H, bs), 6.34-6.37 (1H, dd, J=2.48, 8.56 Hz), 6.70 (1H, d, J=2.46 Hz), 6.90-6.92 (1H, d, J=8.56 Hz);
Mass (m/z): 185.6 (M+H)$^+$.

Step (III): Preparation of N-(4-chloro-3-acetamido phenyl)benzenesulfonamide

To a dry 100 mL three necked round-bottomed flask containing dichloroethane (20 mL) was added 2-chloro-5-amino acetanilide (1.5 grams, 8 mmol) obtained at step (II), followed by addition of pyridine (0.7 mL, 8 mmol) under nitrogen atmosphere. The reaction mass was stirred for 1 hour, then benzene sulfonyl chloride (1.6 mL, 9.2 mmol) was added drop-wise at room temperature in 20 minutes and further stirred the reaction mass for 2 hours. After completion of reaction the reaction mass was quenched into 100 mL water and extracted the product with dichloroethane (3×350 mL). The combined organic layers were washed with saturated brine solution (2×25 mL), dried over anhydrous sodium sulfate, filtered free of salts and concentrated under vacuum to obtain oily mass, which was further purified by column chromatography using ethyl acetate and hexane as eluents to obtain 2.1 grams product.

IR spectra (cm$^{-1}$): 1652, 1522, 1310, 1155;
$^1$H-NMR (δ ppm): 2.1 (3H, s), 3.52 (1H, bs), 6.34-6.37 (1H, dd, J=8.56, 2.48 Hz), 6.70 (1H, d, J=2.46 Hz), 6.90-6.92 (1H, d, J=8.56 Hz), 7.25-7.39 (3H, m), 7.66-7.68 (2H, m), 9.41 (1H, s);
Mass (m/z): 325.7 (M+H)$^+$.

Step (IV): Preparation of N-(4-chloro-3-amino phenyl)benzenesulfonamide

N-(4-chloro-3-acetamido phenyl)benzenesulfonamide (4.5 grams, 13.8 mmol) obtained at step (III) was added to a 100 mL three neck round bottomed flask containing ethanol (50 mL) under stirring. Added an aqueous solution of concentrated hydrochloric acid (4.2 mL, 30 mmol) and heated the reaction mass at reflux (75-80° C.) for 5 hours. Ethanol was distilled off under vacuum and the resulting mass was quenched into water (100 mL) and basified with triethylamine. The product was extracted with ethyl acetate (4×100 mL). The combined organic layers-were washed with saturated brine solution (2×25 mL), dried over anhydrous sodium sulfate, filtered free of salts and concentrated under vacuum to obtain oily mass, which was further purified by column chromatography using ethyl acetate and hexane (1:1 mixture) to obtain 3.1 grams product.

IR spectra (cm$^{-1}$): 1603, 1520, 1325, 1151;

¹H-NMR (δ ppm): 3.96 (2H, bs), 6.35-6.38 (1H, dd, J=8.56, 2.48 Hz), 6.62 (1H, d, J=2.46 Hz), 6.86-6.88 (1H, d, J=8.56 Hz), 7.25-7.39 (3H, m), 7.66-7.68 (2H, m), 9.41 (1H, s);

Mass (m/z): 283.7 (M+H)⁺.

Preparation 2: Preparation of 4-methoxy-N-methyl-N-(1-methyl piperidin-4-yl)benzene-1,3-diamine Step (I): Preparation of 2-Methoxy-5-nitro-N-(1-Boc piperidin-4-yl)phenylamine Added 2-methoxy-5-nitro phenylamine (8.0 grams, 47.61 mmol) to a round bottomed flask, followed by the addition of 1-boc-4-piperidone (28.42 grams, 142.83 mmol), sodium sulfate (67.6 grams, 476 mmol) and acetic acid (80 mL). The above reaction mass was stirred for 8 hours at ambient temperature. Then added sodium triacetoxyborohydride (30.28 grams, 142.83 mmol) at 20-25° C. in 5 minutes and stirred the reaction mass for further 3 hours. The reaction mass was quenched into water (100 mL) and basified to pH: 9 with 50% aqueous sodium hydroxide solution. The product was extracted with ethyl acetate (4×50 mL). Combined organic layer was washed with brine (100 mL), dried over sodium sulfate and concentrated to obtain oily product. The product was further purified by column chromatography, the eluent being ethyl acetate, n-hexane and triethylamine, to obtain 24.01 grams of pure product.

IR spectra (cm⁻¹): 3418, 2950, 1685, 1264, 1172;
¹H-NMR (δ ppm): 1.35-1.45 (2H, m), 1.47 (9H, s), 2.04-2.09 (2H, m), 2.96-3.02 (2H, m), 3.50-3.52 (1H, m), 3.94 (3H, s), 4.06-4.11 (2H, m), 4.33-4.35 (1H, d, J=7.76 Hz), 6.75-6.77 (1H, d, J=8.8 Hz), 7.38-7.39 (1H, d, J=2.64 Hz), 7.60-7.63 (1H, dd, J=8.76, 2.64 Hz);

Mass (m/z): 352.2 (M+H)⁺.

Step (II): Preparation of 2-Methoxy-5-nitro-N-methyl-N-(1-Boc piperidine-4-yl)phenyl amine Placed 2-Methoxy-5-nitro-N-(1-Boc piperidin-4-yl)phenylamine (5 grams, 14.24 mmol) obtained at step (I) into a round bottom flask containing methanol (10 mL) and stirred at 25-30° C. for 5 minutes. Added sodium cyanoborohydride (1.06 grams, 17.09 mmol) and formic acid (1.96 grams, 42.7 mmol) and stirred the reaction mass for 10 minutes. White solid mass separated out. Then the reaction mass was cooled to 0-5° C. in an ice bath and added formaldehyde (2.84 mL, 28.4 mmol, 30-50%). A clear solution was obtained. The mass was further stirred for 6 hours at 20-25° C. After completion of reaction (thin layer chromatography), solvent was distilled off to obtain oily mass. Added water (100 mL) and basified to pH: 8 using saturated solution of sodium bicarbonate solution. Extracted the product with ethyl acetate (3×100 mL) and layers separated. The combined organic layer was washed with brine solution (100 mL) and dried over anhydrous sodium sulfate. The organic layer was concentrated to obtain 5.86 grams of dark yellow colored oil.

IR spectra (cm⁻¹): 3425, 2959, 1680, 1176;
¹H-NMR (δ ppm): 1.45 (9H, s), 1.60-1.69 (4H, m), 2.66 (2H, m), 2.75 (3H, s), 3.34-3.37 (1H, m), 3.94 (3H, s), 4.14-4.19 (2H, bs), 6.88-6.90 (1H, d, J=8.98 Hz), 7.79-7.80 (1H, d, J=2.72 Hz), 7.90-7.93 (1H, dd, J=8.95, 2.72 Hz);

Mass (m/z): 366.5 (M+H)⁺.

Step (III): Preparation of 2-Methoxy-5-nitro-N-methyl-N-(piperidin-4-yl)phenylamine To a 250 mL three neck round bottom flask, added 2-Methoxy-5-nitro-N-methyl-N-(1-Boc piperidine-4-yl)phenyl amine (3 grams, 8.21 mmol) obtained at step (II), followed by the addition of isopropyl alcohol (20 mL) and allowed to stir for 10 minutes. The reaction mass was heated to 40-45° C. and stirred for 5 minutes to get a clear solution. Isopropanolic hydrogenchloride, (20%) solution (15.99 mL, 65.75 mmol) was added to the above reaction mass, drop-wise over a period of 10 minutes. Further the reaction mass was heated at 60-63° C. for 2 hours. The solids that separated were filtered and taken into water (20 mL), basified with ammonia solution and extracted with ethyl acetate (3×50 mL). The combined organic layer was washed with brine solution (20 mL), dried over sodium sulfate and solvent was removed under reduced pressure to obtain 2.5 grams of the title product.

IR spectra (cm⁻¹): 3410, 2956, 1650, 1174;
¹H-NMR (δ ppm): 1.65-1.72 (4H, m), 2.55-2.61 (2H, m), 2.78 (3H, s), 3.14-3.17 (2H, m), 3.31-3.34 (1H, m), 3.94 (3H, s), 6.87-6.89 (1H, d, J=8.96 Hz), 7.79-7.80 (1H, d, J=2.74 Hz); 7.88-7.91 (1H, dd, J=8.98, 2.68 Hz);

Mass (m/z): 266.1 (M+H)⁺.

Step (IV): Preparation of 2-Methoxy-5-nitro-N-methyl-N-(1-methyl piperidin-4-yl)phenylamine To a 250 mL three neck round bottom flask added 2-Methoxy-5-nitro-N-methyl-N-(piperidin-4-yl) phenylamine (1.93 grams, 7.33 mmol) obtained at step (III), followed by the addition of methanol (20 mL) and stirred at 25-30° C. for 5 minutes. Added sodium cyanoborohydride (0.548 grams, 8.80 mmol) and formic acid (1.08 mL, 22.01 mmol) and stirred the reaction mass for 10 minutes. The reaction mass was cooled to 0-5° C. in an ice bath and added formaldehyde (1.46 mL, 14.6 mmol, 30-50%) through syringe. Clear solution was obtained. The reaction mass was further stirred for 6 hours at 20-25° C. After completion of reaction (thin layer chromatography), solvent was distilled off under reduced pressure. To the residual oily mass, added water (100 mL) and basified to pH: 8 using saturated solution of sodium bicarbonate. The product was extracted with ethyl acetate (3×100 mL). The combined organic layer was washed with brine solution (100 mL) and dried over anhydrous sodium sulfate. Solvent was removed under reduced pressure to obtain 1.96 grams of dark yellow colored oily mass.

IR spectra (cm⁻¹): 2956, 1650, 1515, 1180;
¹H-NMR (δ ppm): 1.68-1.71 (2H, m), 1.86-1.92 (2H, m), 1.98-2.04 (2H, m), 2.17 (3H, s), 2.78 (3H, s), 2.94-2.97 (2H, m), 3.25-3.28 (1H, m), 3.96 (3H, s), 6.87-6.91 (1H, d, J=8.98 Hz), 7.80 (1H, d, J=2.68 Hz), 7.88-7.92 (1H, dd, J=8.96, 2.64 Hz);

Mass (m/z): 280.2 (M+H)⁺.

Step (V): Preparation of 4-methoxy-N-methyl-N-(1-methyl piperidin-4-yl)benzene-1,3-diamine To a 250 mL three necked round bottomed flask, added iron powder (1.99 grams, 6.81 mmol) and 10 mL of demineralized water. Stirred the mass for 5 minutes and added concentrated hydrochloric acid (12 mL) drop-wise. The reaction was exothermic. Further, heated the reaction mass to 50° C. and added a solution of 2-methoxy-5-nitro-N-methyl-N-(1-methyl piperidin-4-yl)phenylamine (1.9 grams, 6.81 mmol) obtained at step (IV) was dissolved in ethanol (20 mL), drop-wise through addition funnel. The reaction mass was heated at 78-80° C. for 4 hours. After completion of reaction (thin layer chromatography), ethanol was distilled off completely under reduced pressure to obtain oily mass. Added water (50 mL) and basified to pH: 9 using 50% aqueous sodium hydroxide solution. Filtered the inorganic and washed the cake with ethyl acetate (2×50 mL). The organic layer was separated and dried over anhydrous sodium sulfate and concentrated to obtain 2.31 grams of oily product.

IR spectra (cm$^{-1}$): 3415; 2970, 1625, 1532, 1171;
$^1$H-NMR (δ ppm): 1.24-1.25 (2H, m), 1.68-1.81 (2H, m), 1.92-1.98 (2H, m), 2.26 (3H, s), 2.26-2.27 (2H, m), 2.68 (3H, s), 2.88-2.91 (1H, m), 3.77 (3H, s), 4.70 (2H, bs), 6.29-6.31 (1H, dd, J=8.40, 2.53 Hz), 6.38 (1H, d, J=2.72 Hz), 6.68-6.70 (1H, d, J=8.61 Hz);
Mass (m/z): 250.2 (M+H)$^+$.

Example 1

Preparation of N-[4-Chloro-3-(1-methylpiperidin-4-ylamino)phenyl]benzenesulfonamide N-(4-chloro-3-amino phenyl)benzenesulfonamide (1 gram, 3.5 mmol) obtained at preparation 1 was added to a 100 mL three necked round bottomed flask, followed by addition of 1-methyl-4-Piperidone (0.81 grams, 7.18 mmol), sodium sulfate (3.49 grams, 35 mmol) and acetic acid (20 mL). The reaction mass was stirred for 8 hours at room temperature (30° C.), then sodium triacetoxyborohydride (2.23 grams, 10.5 mmol) was added to the reaction mass at 20-25° C. in 5 minutes. This reaction mixture was further stirred for 3 hours at room temperature. The reaction mixture was quenched into 100 mL water, basified to pH: 9 with 50% aqueous sodium hydroxide solution and extracted the product with ethyl acetate (4×50 mL). The combined organic layers were washed with saturated brine solution (2×50 mL), dried over anhydrous sodium sulfate, and filtered free of salts and concentrated under vacuum to obtain oily mass. It was further purified by column chromatography using ethyl acetate and n-hexane and triethyl amine as an eluents to obtain 0.86 gm of the title product.

IR spectra (cm$^{-1}$): 1603, 1324, 1148, 1092;
$^1$H-NMR (δ ppm): 1.44-1.53 (2H, m), 1.92-1.96 (2H, m), 2.10-2.16 (2H, m), 2.30 (3H, s), 2.76-2.79 (2H, m), 3.18-3.20 (1H, m), 4.18-4.20 (1H, d), 6.17-6.20 (1H, dd, J=8.39, 2.44 Hz), 6.42-6.43 (1H, d, J=2.40 Hz), 7.04-7.06 (1H, d, J=8.39 Hz), 7.43-7.47 (2H, m), 7.53-7.57 (1H, m), 7.76-7.78 (2H, m);
Mass (m/z): 380 (M+H)$^+$.

Examples 2-20

The compounds of Examples 2-20 were prepared by following the procedure as described in Example 1, with some non-critical variations

| | | |
|---|---|---|
| 2. | 4-Fluoro-N-[4-Chloro-3-(1-methylpiperidin-4-ylamino) phenyl] benzenesulfonamide | IR spectra (cm$^{-1}$): 1601, 1520, 1335, 1159; $^1$H-NMR (δ ppm): 1.46-1.55 (2H, m), 1.94-1.98 (2H, m), 2.11-2.17 (2H, m), 2.31 (3H, s), 2.77-2.80 (2H, m), 3.19-3.21 (1H, m), 4.21-4.23 (1H, d), 6.17-6.19 (1H, dd, J = 8.38, 2.46 Hz), 6.42-6.43 (1H, d, J = 2.42 Hz), 7.06-7.08 (1H, d, J = 8.38 Hz), 7.10-7.14 (2H, m), 7.75-7.79 (2H, m); Mass (m/z): 398.2 (M + H)$^+$. |
| 3. | 4-Methyl-N-[4-Chloro-3-(1-methylpiperidin-4-ylamino) phenyl] benzenesulfonamide | IR spectra (cm$^{-1}$): 1603, 1522, 1329, 1151; $^1$H-NMR (δ ppm): 1.44-1.53 (2H, m), 1.93-1.97 (2H, m), 2.11-2.16 (2H, m), 2.31 (3H, s), 2.39 (3H, s), 2.77-2.79 (2H, m), 3.19-3.21 (1H, m), 4.17-4.19 (1H, d), 6.17-6.20 (1H, dd, J = 8.38, 2.42 Hz), 6.43 (1H, d, J = 2.39 Hz), 7.04-7.06 (1H, d, J = 8.4 Hz), 7.22-7.25 (2H, d, J = 8.32 Hz), 7.64-7.66 (2H, d, J = 8.29 Hz); Mass (m/z): 394.2 (M + H)$^+$. |
| 4. | 4-Isopropyl-N-[4-Chloro-3-(1-methylpiperidin-4-ylamino) phenyl] benzenesulfonamide | IR spectra (cm$^{-1}$): 1602, 1328, 1153, 1095; $^1$H-NMR (δ ppm): 1.21-1.23 (6H, d, J = 6.92 Hz), 1.46-1.52 (2H, m), 1.91-1.96 (2H, m), 2.10-2.15 (2H, m), 2.29 (3H, s), 2.75-2.77 (2H, m), 2.91-2.94 (1H, septet, J = 6.92 Hz), 3.18-3.20 (1H, m), 4.17-4.19 (1H, d, J = 7.76 Hz), 6.19-6.21 (1H, dd, J = 8.40, 2.48 Hz), 6.43 (1H, d, J = 2.40 Hz), 7.03-7.05 (1H, d, J = 8.40 Hz), 7.27-7.29 (2H, m), 7.67-7.69 (2H, m); Mass (m/z): 422.3 (M + H)$^+$. |
| 5. | 2-Bromo-N-[4-Chloro-3-(1-methylpiperidin-4-ylamino) phenyl] benzenesulfonamide | IR spectra (cm$^{-1}$): 1603, 1517, 1337, 1161; $^1$H-NMR (δ ppm): 1.50-1.56 (2H, m), 1.95-1.98 (2H, m), 2.19-2.25 (2H, m), 2.35 (3H, s), 2.83-2.85 (2H, m), 3.23 (1H, m), 4.16-4.18 (1H, d, J = 7.52 Hz), 6.29-6.32 (1H, dd, J = 8.40, 2.44 Hz), 6.48-6.49 (1H, d, J = 2.40 Hz), 7.02-7.04 (1H, d, J = 8.4 Hz), 7.37-7.39 (2H, m), 7.69-7.71 (1H, m), 8.00-8.02 (1H, m); Mass (m/z): 458, 460 (M + H)$^+$. |
| 6. | 4-Fluoro-N-[4-Methoxy-3-(1-methylpiperidin-4-ylamino) phenyl] benzenesulfonamide | IR spectra (cm$^{-1}$): 1525, 1343, 1223, 1163; $^1$H-NMR (δ ppm): 1.47-1.52 (2H, m), 1.93-1.97 (2H, m), 2.11-2.17 (2H, m), 2.32 (3H, s), 2.82-2.85 (2H, m), 3.12-3.14 (1H, m), 3.78 (3H, s), 4.11-4.13 (1H, m), 6.18-6.21 (1H, dd, J = 8.40, 2.48 Hz), 6.30-6.31 (1H, d, J = 2.44 Hz), 6.54-6.56 (1H, d, J = 8.44 Hz), 7.07-7.11 (2H, m), 7.70-7.73 (2H, m); Mass (m/z): 394.2 (M + H)$^+$. |
| 7. | N-[4-Methoxy-3-(1-methylpiperidin-4-ylamino) phenyl] benzenesulfonamide | IR spectra (cm$^{-1}$): 1607, 1525, 1339, 1223, 1148; $^1$H-NMR (δ ppm): 1.40-1.49 (2H, m), 1.90-1.97 (2H, m), 2.01-2.12 (2H, m), 2.30 (3H, s), 2.78-2.81 (2H, m), 3.10 (1H, m), 3.78 (3H, s), 4.11 (1H, m), 6.20-6.23 (1H, dd, J = 8.36, 2.48 Hz), 6.29 (1H, d, J = 2.48 Hz), 6.53-6.56 (1H, d, J = 8.40 Hz), 7.40-7.44 (2H, m), 7.50-7.54 (1H, m), 7.71-7.73 (2H, m); Mass (m/z): 376.2 (M + H)$^+$. |

| | | |
|---|---|---|
| 8. | 2-Bromo-N-[4-Methoxy-3-(1-methylpiperidin-4-ylamino) phenyl] benzenesulfonamide | IR spectra (cm$^{-1}$): 1521, 1346, 1227, 1164;<br>$^1$H-NMR (δ ppm): 1.36-1.45 (2H, m), 1.87-1.91 (2H, m), 2.03-2.12 (2H, m), 2.30 (3H, s), 2.77-2.80 (2H, m), 3.08 (1H, m), 3.73 (3H, s), 4.05-4.07 (1H, m), 6.32-6.35 (2H, m), 6.49-6.52 (1H, d, J = 8.92 Hz), 7.32-7.34 (2H, m), 7.69-7.71 (1H, m), 7.93-7.95 (1H, m);<br>Mass (m/z): 454, 456 (M + H)$^+$. |
| 9. | 4-Isopropyl-N-[4-Methoxy-3-(1-methylpiperidin-4-ylamino) phenyl] benzenesulfonamide | IR spectra (cm$^{-1}$): 1521, 1324, 1167, 1220;<br>$^1$H-NMR (δ ppm): 1.22-1.24 (6H, d, 6.92 Hz), 1.44-1.50 (2H, m), 1.92-1.95 (2H, m), 2.07-2.12 (2H, m), 2.29 (3H, s), 2.76-2.79 (2H, m), 2.91-2.94 (1H, septet), 3.11 (1H, m), 3.78 (3H, s), 4.11-4.13 (1H, m), 6.23-6.26 (1H, dd, J = 8.40, 2.48 Hz), 6.30-6.31 (1H, d, J = 2.40 Hz), 6.55-6.57 (1H, d, J = 8.40 Hz), 7.25-7.27 (2H, m), 7.63-7.65 (2H, m);<br>Mass (m/z): 418.4 (M + H)$^+$. |
| 10. | 4-Methyl-N-[4-Methoxy-3-(1-methylpiperidin-4-ylamino) phenyl] benzenesulfonamide | IR spectra (cm$^{-1}$): 1607, 1525, 1338, 1224, 1150;<br>$^1$H-NMR (δ ppm): 1.40-1.49 (2H, m), 1.90-1.93 (2H, m), 2.00-2.09 (2H, m), 2.30 (3H, s), 2.38 (3H, s), 2.76-2.79 (2H, m), 3.10 (1H, m), 3.77 (3H, s), 4.09-4.11 (1H, m), 6.21-6.23 (1H, dd, J = 8.36, 2.47 Hz), 6.28 (1H, d, J = 2.46 Hz), 6.54-6.56 (1H, d, J = 8.4 Hz), 7.19-7.20 (2H, m), 7.59-7.61 (2H, m);<br>Mass (m/z): 390.3 (M + H)$^+$. |
| 11. | 2-Bromo-N-[3-(1-methylpiperidin-4-ylamino) phenyl] benzenesulfonamide | IR spectra (cm$^{-1}$): 1518, 1427, 1331, 1154;<br>$^1$H-NMR (δ ppm): 1.41-1.47 (2H, m), 1.92-1.96 (2H, m), 2.11-2.13 (2H, m), 2.30 (3H, s), 2.78-2.81 (2H, m), 3.16-3.18 (1H, m), 6.27-6.30 (1H, dd, J = 8.10, 2.02 Hz), 6.35-6.37 (1H, m), 6.40-6.41 (1H, m), 6.92-6.96 (1H, t, J = 8.01 Hz), 7.34-7.37 (2H, m), 7.68-7.70 (1H, m), 8.03-8.05 (1H, m);<br>Mass (m/z): 424, 426 (M + H)$^+$. |
| 12. | 4-Isopropyl-N-[3-(1-methylpiperidin-4-ylamino) phenyl] benzenesulfonamide | IR spectra (cm$^{-1}$): 1159, 1331, 1608;<br>$^1$H-NMR (δ ppm): 1.22-1.24 (6H, d, J = 6.92 Hz), 1.38-1.48 (2H, m), 1.95-1.98 (2H, m), 2.07-2.12 (2H, m), 2.29 (3H, s), 2.77-2.80 (2H, m), 2.89-2.94 (1H, septet, J = 6.92 Hz), 3.17-3.19 (1H, m), 3.55-3.57 (1H, d), 6.24-6.27 (1H, dd, J = 7.78, 1.67 Hz), 6.30-6.33 (1H, dd, J = 8.14, 1.94 Hz), 6.37-6.38 (1H, t, J = 7.99 Hz), 6.95-6.99 (1H, t), 7.26-7.28 (2H, m), 7.69-7.71 (2H, m);<br>Mass (m/z): 388.4 (M + H)$^+$. |
| 13. | 4-Fluoro-N-[3-(1-methylpiperidin-4-ylamino) phenyl] benzenesulfonamide | IR spectra (cm$^{-1}$): 1600, 1329, 1271, 1221, 1158;<br>$^1$H-NMR (δ ppm): 1.42-1.51 (2H, m), 1.96-2.04 (2H, m), 2.11-2.16 (2H, m), 2.31 (3H, s), 2.82-2.85 (2H, m), 3.17-3.22 (1H, m), 6.24-6.26 (1H, m), 6.32-6.37 (2H, m), 6.95-6.99 (1H, t, J = 8.0 Hz), 7.08-7.12 (2H, m), 7.76-7.80 (2H, m);<br>Mass (m/z): 364.5 (M + H)$^+$. |
| 14. | 4-Methyl-N-[3-(1-methylpiperidin-4-ylamino) phenyl] benzenesulfonamide | IR spectra (cm$^{-1}$): 1595, 1513, 1328, 1151;<br>$^1$H-NMR (δ ppm): 1.39-1.40 (2H, m), 1.94-1.98 (2H, m), 2.04-2.13 (2H, m), 2.29 (3H, s), 2.37 (3H, s), 2.77-2.80 (2H, m), 3.17 (1H, bs), 3.55 (1H, bs), 6.23-6.26 (1H, dd, J = 7.65, 1.49 Hz), 6.30-6.32 (1H, dd, J = 8.09, 1.82 Hz), 6.36-6.37 (1H, t, J = 2.11 Hz), 6.94-6.98 (1H, t, J = 8.0 Hz), 7.21-7.23 (2H, m), 7.65-7.67 (2H, m);<br>Mass (m/z): 360.3 (M + H)$^+$. |
| 15. | 2-Bromo-N-[4-Methyl-3-(1-methylpiperidin-4-ylamino) phenyl] benzenesulfonamide | IR spectra (cm$^{-1}$): 1516, 1436, 1319, 1159;<br>$^1$H-NMR (δ ppm): $^1$H-NMR (δ ppm): 1.37-1.46 (2H, m), 1.92-1.94 (2H, m), 1.96 (3H, s), 2.11-2.16 (2H, m), 2.31 (3H, s), 2.78-2.80 (2H, m), 3.18 (1H, s), 3.31 (1H, m), 6.30-6.32 (1H, dd, J = 7.84, 2.12 Hz), 6.38-6.39 (1H, d, J = 2.08 Hz), 6.80-6.82 (1H, d), 7.33-7.35 (2H, m), 7.67-7.69 (1H, m), 7.98-8.01 (1H, m);<br>Mass (m/z): 438, 440 (M + H)$^+$. |
| 16. | N-[4-Methyl-3-(1-methylpiperidin-4-ylamino) phenyl] benzenesulfonamide | IR spectra (cm$^{-1}$): 1614, 1523, 1329, 1159;<br>$^1$H-NMR (δ ppm): 1.39-1.49 (2H, m), 1.94-1.97 (2H, m), 2.01 (3H, s), 2.04-2.14 (2H, m), 2.31 (3H, s), 2.77-2.80 (2H, m), 3.19-3.21 (1H, m), 3.30-3.45 (1H, m), 6.18-6.21 (1H, dd), 6.35 (1H, d), 6.84-6.86 (1H, d), 7.41-7.45 (2H, m), 7.50-7.54 (1H, m), 7.75-7.77 (2H, m);<br>Mass (m/z): 360.3 (M + H)$^+$. |
| 17. | 4-Fluoro-N-[4-Methyl-3-(1-Methylpiperidin-4-ylamino) phenyl] benzenesulfonamide | IR spectra (cm$^{-1}$): 1592, 1523, 1334, 1162, 1153;<br>$^1$H-NMR (δ ppm): 1.42-1.51 (2H, m), 1.96-1.99 (2H, m), 2.01 (3H, s), 2.04-2.16 (2H, m), 2.31 (3H, s), 2.79-2.82 (2H, m), 3.20 (1H, m), 3.40 (1H, bs), 6.17-6.20 (1H, dd, J = 8.4, 2.40 Hz), 6.34-6.35 (1H, d, J = 2.44 Hz), |

| | -continued |
|---|---|
| | 6.85-6.87 (1H, d, J = 8.40 Hz), 7.07-7.12 (2H, m), 7.74-7.78 (2H, m); Mass (m/z): 378.2 (M + H)⁺. |
| 18. 4-Methyl-N-[4-Methyl-3-(1-Methylpiperidin-4-ylamino) phenyl] benzenesulfonamide | IR spectra (cm⁻¹): 1615, 1523, 1330, 1156; ¹H-NMR (δ ppm): 1.44-1.52 (2H, m), 1.86-2.01 (2H, m), 2.02 (3H, s), 2.14-2.19 (2H, m), 2.33 (3H, s), 2.38 (3H, s), 2.80-2.85 (2H, m), 3.19-3.21 (1H, m), 6.17-6.19 (1H, dd, J = 7.82, 1.93, Hz), 6.35-6.36 (1H, d, J = 1.76 Hz), 6.84-6.86 (1H, d, J = 7.84 Hz), 7.20-7.22 (2H, m), 7.63-7.65 (2H, m); Mass (m/z): 374.3 (M + H)⁺. |
| 19. N-[3-(1-methylpiperidin-4-ylamino) phenyl] benzenesulfonamide | IR spectra (cm⁻¹): 1608, 1327, 1156; ¹H-NMR (δ ppm): 1.53-1.56 (2H, m), 1.97-2.04 (2H, m), 2.24-2.29 (2H, m), 2.38 (3H, s), 2.94-2.97 (2H, d), 3.22-3.20 (1H, m), 6.24-6.26 (1H, m), 6.30-6.33 (1H, m), 6.39 (1H, bs), 6.94-6.98 (1H, t, J = 8.04 Hz), 7.41-7.45 (2H, m), 7.51-7.53 (1H, m), 7.70-7.78 (2H, m); Mass (m/z): 346.2 (M + H)⁺. |
| 20. 5-Chloro-3-methyl-N-[4-methoxy-3-(1-methylpiperidin-4-ylamino) phenyl] benzo[b]thiophene-2-yl sulfonamide | IR spectra (cm⁻¹): 1527, 1322, 1154; ¹H-NMR (δ ppm): 1.50-1.58 (2H, m), 1.87-1.90 (2H, m), 2.18-2.23 (2H, t), 2.31 (3H, s), 2.40 (3H, s), 2.94-2.97 (2H, m), 3.05-3.10 (1H, m), 3.78 (3H, s), 4.11-4.13 (2H, bs), 6.27-6.29 (2H, m), 6.54-6.56 (1H, d, J = 8.9 Hz), 7.42-7.45 (1H, dd, J = 8.60, 1.90 Hz), 7.69 (1H, d, J = 1.60 Hz), 7.71-7.74 (1H, d, J = 8.60 Hz); Mass (m/z): 480.5 (M + H)⁺. |

Example 21

Preparation of N-[4-Chloro-3-(1-methylpiperidin-4-ylamino)phenyl]benzenesulfonamide hydrochloride The product (0.86 grams) obtained from Example 1 was converted into its hydrochloride salt by using the following procedure. The obtained base was taken into diethyl ether (25 mL) and added 1 mL of 10% isopropanolic hydrogen chloride. The reaction mass was stirred for 3 hours at 25-30° C. and filtered the hydrochloride salt to obtain the title product (0.8 grams).

IR spectra (cm⁻¹): 1605, 1326, 1152, 1095;
¹H-NMR (δ ppm): 1.46-1.50 (2H, m), 1.94-1.97 (2H, m), 2.12-2.15 (2H, m), 2.32 (3H, s), 2.75-2.78 (2H, m), 3.19-3.21 (1H, m), 4.15-4.17 (1H, d), 6.19-6.21 (1H, dd, J=8.39, 2.44 Hz), 6.44-6.45 (1H, d, J=2.40 Hz), 7.08-7.10 (1H, d, J=8.39 Hz), 7.44-7.48 (2H, m), 7.54-7.56 (1H, m), 7.78-7.80 (2H, m);
Mass (m/z): 380 (M+H)⁺.

Example 22

Preparation of 4-Isopropyl-N-[4-Methyl-3-(1-Methylpiperidin-4-ylamino) phenyl]benzenesulfonamide hydrochloride 4-Isopropyl-N-[4-Methyl-3-(1-Methylpiperidin-4-ylamino)phenyl]benzenesulfonamide is prepared by using similar producure as mentioned in Example 1, with some non-critical variations. The base, thus obtained, was taken into diethyl ether (25 mL) and added 1 mL of 10% isopropanolic hydrogen chloride. The reaction mass was stirred for 3 hours at 25-30° C. and filtered the hydrochloride salt to obtain the title product (0.78 grams)

IR spectra (cm⁻¹): 1592, 1528, 1166, 1156;
¹H-NMR (δ ppm): 1.22-1.24 (6H, d, J=6.92 Hz), 1.43-1.48 (2H, m), 1.95-1.97 (2H, m), 2.02 (3H, s), 2.10-2.15 (2H, m), 2.30 (3H, s), 2.77-2.79 (2H, m), 2.91-2.94 (1H, septet, J=6.92 Hz), 3.20 (1H, m), 3.40 (1H, bs), 6.20-6.23 (1H, dd, J=8.40, 2.40 Hz), 6.36-6.37 (1H, d, J=2.40 Hz), 6.85-6.87 (1H, d, J=8.40 Hz), 7.26-7.28 (2H, m), 7.67-7.70 (2H, m);
Mass (m/z): 402.3 (M+H)⁺.

Example 23

Preparation of 2-Bromo-N-{4-methoxy-3-[N-methyl-N-(1-methyl piperidin-4-yl)amino] phenyl}benzenesulfonamide 4-Methoxy-N-methyl-N-(1-methyl piperidin-4-yl)benzene-1,3-diamine (2 grams, 8.03 mmol) obtained at preparation 2 was dissolved in dichloromethane (25 mL) in a 100 mL flask. Pyridine (1.29 mL, 16.06 mmol) was added to the flask and stirred the reaction mass under nitrogen atmosphere for 30 minutes. Added a solution of 2-bromo benzenesulfonylchloride (2.45 grams, 9.63 mmol) in dichloromethane (10 mL), drop-wise through a dropping funnel at 25-30° C. The reaction mass was further stirred for 4 hours. Added water (80 mL) and extracted the product with dichloromethane (3×60 mL). Combined organic layer was dried and solvent removed under reduced pressure to obtain oily mass. Further, it was purified column chromatography using ethyl acetate and hexane as an eluents to obtain the title product (1.65 grams).

Melting range: 119.2-121.3° C.;
IR spectra (cm⁻¹): 2951, 1503, 1330, 1235, 1164;
¹H-1-NMR (δ ppm): 1.46-1.49 (2H, m), 1.64-1.71 (2H, m), 1.83-1.89 (2H, m), 2.24 (3H, s), 2.54 (3H, s), 2.83-2.86 (2H, m), 3.08 (1H, m), 3.76 (3H, s), 6.64-6.68 (2H, m), 6.75-6.78 (1H, dd, J=8.60, 2.53 Hz), 7.28-7.36 (2H, m), 7.70-7.72 (1H, dd, J=7.6, 1.6 Hz), 7.89-7.99 (1H, dd, J=7.42, 2.08 Hz);
Mass (m/z): 468.2, 470.2 (M+H)⁺.

Examples 24-47

The person skilled in the art can prepare the compounds of Examples 24-47 by following the procedures described above.

24. N-[4-Bromo-3-(1-methylpiperidin-4-ylamino) phenyl] benzenesulfonamide;
25. N-[4-Ethoxy-3-(1-methylpiperidin-4-ylamino) phenyl] benzenesulfonamide;
26. N-[4-Trifluoromethyl-3-(piperidin-4-ylamino) phenyl] benzenesulfonamide;
27. 4-Fluoro-N-[4-fluoro-3-(1-methylpiperidin-4-ylamino) phenyl] benzenesulfonamide;
28. 4-Fluoro-N-[4-Methoxy-3-(piperidin-1-ylamino) phenyl] benzenesulfonamide;
29. 4-Methyl-N-[4-bromo-3-(1-methylpiperidin-4-ylamino) phenyl] benzenesulfonamide;
30. 4-Methyl-N-[4-ethoxy-3-(piperidin-1-ylamino) phenyl] benzenesulfonamide;
31. 4-Isopropyl-N-[4-trifluoromethoxy-3-(1-methylpiperidin-4-ylamino) phenyl] benzenesulfonamide;
32. 4-Isopropyl N-[4-Chloro-3-(piperidin-1-ylamino) phenyl] benzenesulfonamide;
33. 2-Bromo-N-[4-Chloro-3-(piperidin-1-ylamino) phenyl] benzenesulfonamide;
34. 4-Bromo-N-[3-(1-methylpiperidin-4-ylamino) phenyl] benzenesulfonamide;
35. 4-Bromo-N-[4-chloro-3-(1-methylpiperidin-4-ylamino) phenyl] benzenesulfonamide;
36. 4-Methoxy-N-[4-bromo-3-(1-methylpiperidin-4-ylamino) phenyl] benzenesulfonamide;
37. 4-Methoxy-N-[4-trifluoromethyl-3-(piperidin-1-ylamino) phenyl] benzenesulfonamide;
38. 2,4-Dichloro-N-[4-methoxy-3-(1-methylpiperidin-4-ylamino) phenyl] benzenesulfonamide;
39. 2,4-Dichloro-N-[4-bromo-3-(piperidin-1-ylamino) phenyl] benzenesulfonamide;
40. 4-Trifluoromethoxy-N-[4-chloro-3-(1-methylpiperidin-4-ylamino) phenyl] benzenesulfonamide;
41. 4-chloro-N-[4-Chloro-3-(piperidin-1-ylamino) phenyl] benzenesulfonamide;
42. 2-Chloro-N-[4-chloro-3-(1-methylpiperidin-4-ylamino) phenyl] benzenesulfonamide;
43. 2-Methoxy-N-[4-trifluoromethyl-3-(piperidin-1-ylamino) phenyl] benzenesulfonamide;
44. 4-Methyl-N-[4-Chloro-3-[N-methyl-N-(4-methylpiperidin-1-yl)amino] phenyl] benzenesulfonamide;
45. 4-Methyl-N-[4-Methoxy-3-[N-methyl-N-(4-methylpiperidin-1-yl)amino] phenyl] benzenesulfonamide;
46. 4-Methyl-N-[4-fluoro-3-[N-methyl-N-(piperidin-1-yl)amino] phenyl] benzenesulfonamide;
47. 4-Methyl-N-[4-trifluoromethyl-3-[N-methyl-N-(piperidin-1-yl)amino] phenyl] benzenesulfonamide;

Example 48

Tablet Comprising a Compound of Formula (I)

| Ingredient | Amount |
| --- | --- |
| Compound according to example1 | 5 mg |
| Lactose | 60 mg |
| Crystalline cellulose | 25 mg |
| K 90 Povidone | 5 mg |
| Pregelatinised starch | 3 mg |
| Colloidal silicon dioxide | 1 mg |
| Magnesium stearate | 1 mg |
| Total weight per tablet | 100 mg |

The ingredients were combined and granulated using a solvent such as methanol. The formulation was then dried and formed into tablets (containing about 20 mg of active compound) with an appropriate tablet machine.

Example 49

Composition for Oral Administration

| Ingredient | % wt./wt. |
| --- | --- |
| Active ingredient | 20.0% |
| Lactose | 79.5% |
| Magnesium stearate | 0.5% |

The ingredients were mixed and dispensed into capsules containing about 100 mg each; one capsule would approximate a total daily dosage.

Example 50

Liquid Oral Formulation

| Ingredient | Amount |
| --- | --- |
| Active ingredient | 1.0 gm |
| Fumaric acid | 0.5 gm |
| Sodium chloride | 2.0 gm |
| Methyl paraben | 0.15 gm |
| Propyl paraben | 0.05 gm |
| Granulated sugar | 25.5 gm |
| Sorbitol (70% solution) | 12.85 gm |
| Veegum K (Vanderbilt Co.) | 1.0 gm |
| Flavoring | 0.035 gm |
| Coloring | 0.5 gm |
| Distilled water | q.s. to 100 mL |

The ingredients were mixed to form a suspension for oral administration.

Example 51

Parenteral Formulation

| Ingredient | % wt./wt. |
| --- | --- |
| Active ingredient | 0.25 gm |
| Sodium Chloride | qs to make isotonic |
| Water for injection | 100 mL |

The active ingredient was dissolved in a portion of the water for injection. A sufficient quantity of sodium chloride was then added with stirring to make the solution isotonic. The solution was made up to weight with the remainder of the water for injection, filtered through a 0.2 micron membrane filter and packaged under sterile conditions.

Example 52

Suppository Formulation

| Ingredient | % wt./wt. |
|---|---|
| Active ingredient | 1.0% |
| Polyethylene glycol 1000 | 74.5% |
| Polyethylene glycol 4000 | 24.5% |

The ingredients were melted together and mixed on a steam bath and poured into molds containing 2.5 grams total weight.

Example 53

Topical Formulation

| Ingredients | gm |
|---|---|
| Active ingredient | 0.2-2 gm |
| Span 60 | 2 gm |
| Tween 60 | 2 gm |
| Mineral oil | 5 gm |
| Petrolatum | 10 gm |
| Methyl paraben | 0.15 gm |
| Propyl paraben | 0.05 gm |
| BHA (butylated hydroxy anisole) | 0.01 gm |
| Water | 100 mL |

All of the ingredients, except water, were combined and heated to about 60° C. with stirring. A sufficient quantity of water at about 60° C. was then added with vigorous stirring to emulsify the ingredients and then water added q.s about 100 grams.

Example 54

Binding Assay for Human 5-HT$_6$ Receptor

Compounds can be tested according to the following the procedures.
Materials and Methods:
Receptor source: Human recombinant expressed in HEK293 cells
Radioligand: [$^3$H]LSD (60-80 Ci/mmol)
Final ligand concentration— [1.5 nM]
Non-specific determinant: Methiothepin mesylate— [0.1 μM]
Reference compound: Methiothepin mesylate
Positive control: Methiothepin mesylate
Incubation Conditions:
Reactions were carried out in 50 μM TRIS-HCl (pH 7.4) containing 10 μM MgCl$_2$, 0.5 mM EDTA for 60 minutes at 37° C. The reaction was terminated by rapid vacuum filtration onto glass fiber filters. Radioactivity trapped onto the filters was determined and compared to control values in order to ascertain any interactions of test compound(s) with the cloned serotonin 5-HT$_6$ binding site.

| Example Number | % Inhibition at 10 nM | % Inhibition at 100 nM | % Inhibition at 1000 nM |
|---|---|---|---|
| 2. | — | 69.45 | 96.73 |
| 3. | — | 78.66 | 98.42 |
| 5. | — | 93.8 | 101.6 |
| 6. | 20.71 | 90.83 | 99.64 |
| 8. | 71.95 | 99.38 | 100.63 |
| 10. | — | 88.26 | 99.2 |
| 11. | 8.56 | 64.11 | 94.73 |
| 13. | — | 34.95 | 71.2 |
| 14. | — | 45.25 | 80.78 |
| 15. | — | 99.44 | 104.28 |
| 17. | — | 64.27 | 93.00 |
| 18. | — | 63.42 | 92.37 |

Literature Reference: Monsma F. J. Jr., et al., Molecular Cloning and Expression of Novel Serotonin Receptor with High Affinity for Tricyclic Psychotropic Drugs. Mol. Pharmacol. 1993, 43, 320-327

Example 55

5-HT$_6$ Functional Assay Cyclic AMP

The antagonist property of the compounds at the human 5-HT$_6$ receptors was determined by testing their effect on cAMP accumulation in stably transfected HEK293 cells. Binding of an agonist to the human 5-HT$_6$ receptor will lead to an increase in adenyl cyclase activity. A compound that is an agonist will show an increase in cAMP production and a compound that is an antagonist will block the agonist effect.

Human 5-HT$_6$ receptors were cloned and stably expressed in HEK293 cells. These cells were plated in 6 well plates in DMEM/F12 media with 10% fetal calf serum (FCS) and 500 μg/mL G418 and incubated at 37° C. in a CO$_2$ incubator. The cells were allowed to grow to about 70% confluence before initiation of the experiment. On the day of the experiment, the culture media was removed and the cells were washed once with serum free medium (SFM). Two mL of SFM+IBMX media was added and incubated at 37° C. for 10 minutes. The media were removed and fresh SFM+IBMX media containing various compounds and 1 μM serotonin (as antagonist) were added to the appropriate wells and incubated for 30 minutes. Following incubation, the media were removed and the cells were washed once with 1 mL of PBS (phosphate buffered saline). Each well was treated with 1 mL cold 95% ethanol and 5 μM EDTA (2:1) at 4° C. for 1 hour. The cells were then scraped and transferred into Eppendorf tubes. The tubes were centrifuged for 5 minutes at 4° C. and the supernatants were stored at 4° C. until assayed.

cAMP content was determined by EIA (enzyme-immunoassay) using the Amersham Biotrak cAMP EIA kit (Amersham RPN 225). The procedure used is as described for the kit. Briefly, cAMP is determined by the competition between unlabeled cAMP and a fixed quantity of peroxidase-labelled cAMP for the binding sites on anti-cAMP antibody. The antibody is immobilized onto polystyrene microtitre wells precoated with a second antibody. The reaction is started by adding 50 μL, peroxidase-labeled cAMP to the sample (100 μL) pre-incubated with the antiserum (100 mL) for 2 hours at 4° C. Following 1 hour incubation at 4° C., the unbound ligand is separated by a simple washing procedure. Then an enzyme substrate, trimethylbenzidine (1), is added and incubated at room temperature for 60 minutes. The reaction is stopped by the addition of 100 mL 1.0 M sulphuric acid and the resultant color read by a microtitre plate spectrophotometer at 450 nm within 30 minutes.

In the functional adenylyl cyclase assay, some of the compound of this invention was found to be a competitive antagonist with good selectivity over a number of other receptors including other serotonin receptors such as 5-$HT_{1A}$ and 5-$HT_7$.

Example 56

Rodent Pharmacokinetic Study

Male wistar rats (230-280 grams) obtained from NIN (National Institute of Nutrition, Hyderabad, India) were used as an experimental animal.

Three to five animals were housed in each cage. Animals were kept fasted over night and maintained on a 12 hours light/dark cycle. Three rats were dosed NCE (10 mg/Kg) orally and intravenously on day 0 and day 2

At each time point blood was collected by jugular vein. Plasma was stored frozen at −20° C. until analysis. The concentrations of the NCE compound in plasma were determined using LC-MS/MS method.

Schedule time points: Pre dose. 0.25, 0.5, 1, 1.5, 2, 3, 4, 6, 8, 10, 12 and 24 hours after dosing (n=3). The NCE compounds were quantified in plasma by validated LC-MS/MS method using solid phase extraction technique. NCE compounds were quantified in the calibration range of 2-2000 ng/mL in plasma. Study samples were analyzed using calibration samples in the batch and quality control samples spread across the batch.

Pharmacokinetic parameters $C_{max}$, $T_{max}$, $AUC_t$, $AUC_{inf}$, half life, volume of distribution, clearance, mean residence time and thereby oral bioavailability were calculated by non-compartmental model using software WinNonlin version 5.1.

infusion components (Instech Solomon; Plymouth Meeting, Pa. USA) and allowed free access to food and water NCE compound was dissolved in water and administered at a constant infusion rate (5 mL/kg/hr) over 6-10 hours at a target dose rate of 1.0 mg free base/kg/h. Blood samples were removed during the latter part of the infusion to confirm steady-state blood concentrations, brain and blood was collected and estimated. Animals will be sacrificed to collect the plasma and brain tissue and was homogenized. Plasma and Brain was stored frozen at −20° C. until analysis. The concentrations of the NCE compound in plasma and Brain were determined using LC-MS/MS method.

The NCE compounds were quantified in plasma and brain homogenate by validated LC-MS/MS method using solid phase extraction technique. NCE compounds were quantified in the calibration range of 1-500 ng/mL in plasma and brain homogenate. Study samples were analyzed using calibration samples in the batch and quality control samples spread across the batch. Extents of brain-blood ratio were calculated ($C_b/C_p$).

| Example Number | Strain/Sex | Dose (mg/kg) | Vehicle | Route of administration | Steady State Brain Penetration ($C_b/C_p$) |
|---|---|---|---|---|---|
| 6. | Wistar/Male | 1 | 50% PEG-400 in water for injection | Intravenous | 0.05 ± 0.01 |
| 8. | Wistar/Male | 1 | 50% PEG-400 in water for injection | Intravenous | 0.04 ± 0.01 |
| 15. | Wistar/Male | 1 | 50% PEG-400 in water for injection | Intravenous | 0.35 ± 0.08 |

| Example Number | Strain/Sex | Dose (mg/kg) | Vehicle | Route of administration | $C_{max}$ (ng/mL) | $T_{max}$ (h) | $AUC_t$ (ng · hr/mL) | $T_{1/2}$ (h) | Bioavailability (%) |
|---|---|---|---|---|---|---|---|---|---|
| 6. | Wistar/Male | 10 | 50% PEG-400 in water for injection | Oral | 372 ± 85 | 2.17 ± 1.44 | 1421 ± 106 | 5.35 ± 3.65 | 34 |
|  | Wistar/Male | 10 | 50% PEG-400 in water for injection | Intravenous | 2885 ± 401 | 0.14 ± 0.10 | 4314 ± 967 | 2.18 ± 1.29 |  |
| 8. | Wistar/Male | 10 | 50% PEG-400 in water for injection | Oral | 964 ± 110 | 1.67 ± 1.15 | 6222 ± 1025 | 5.40 ± 2.56 | 63 |
|  | Wistar/Male | 10 | 50% PEG-400 in water for injection | Intravenous | 2645 ± 154 | 0.08 ± 0.0 | 9919 ± 701 | 2.18 ± 0.54 |  |
| 15. | Wistar/Male | 10 | 50% PEG-400 in water for injection | Oral | 503 ± 263 | 2.33 ± 1.15 | 2462 ± 901 | 3.15 ± 2.99 | 99 |
|  | Wistar/Male | 5 | 50% PEG-400 in water for injection | Intravenous | 727 ± 18 | 0.08 ± 0.0 | 1231 ± 52 | 3.08 ± 2.11 |  |

Example 57

Rodent Brain Penetration Study

Male Wister rats (230-280 grams) obtained from NIN (National Institute of Nutrition, Hyderabad, India) was used as an experimental animal. Three animals were housed in each cage. Animals were given water and food ad libitum throughout the experiment, and maintained on a 12 hours light/dark cycle.

Brain penetration was determined at steady state in rat. One day prior to dosing day, male wistar rats (225-250 grams) were anesthetized with halothane for surgical placement of jugular and femoral vein catheters. After surgery, the rats were housed in individual rat infusion cage connected with Example 58

Rodent Brain Micro Dialysis Study for Possible Modulation of Neurotransmitters

Male Wister rats (230-280 grams) obtained from N. I. N. (National Institute of Nutrition, Hyderabad, India) was used as experimental animals.

Group allocation Group 1: Vehicle (Water; 5 mL/kg; p.o.), Group 2: NCE (3 mg/kg; p.o.), Group 3: NCE (10 mg/kg; p.o.)

Surgical Procedure: Rats were anesthetized with chloral hydrate and placed in Stereotaxic frame. Guide cannula (CMA/12) was placed at AP: −5.2 mm, ML: +5.0 mm relative from bregramsa and DV: −3.8 mm from the brain surface according to the atlas of Paxinos and Watson (1986). While the animal was still anesthetized, a micro dialysis probe (CMA/12, 4 mm, PC) was inserted through the guide cannula and secured in place. After surgery recovery period of 48-72 hours was maintained before subjecting the animal for study.

A day prior to study animals were transferred to home cages for acclimatization and implanted probe was perfused overnight with a modified Ringer's solution comprised of: 1.3 µM CaCl2 (Sigramsa), 1.0 µM MgCl$_2$ (Sigramsa), 3.0 µM KCl (Sigramsa), 147.0 µM NaCl (Sigramsa), 1.0 µM Na$_2$HPO$_4$.7H$_2$O and 0.2 µM NaH$_2$PO$_4$.2 H$_2$O and 0.3 µM neostigramsine bromide (Sigramsa) (pH to 7.2) at a rate of 0.2 µL/minutes set by a microinfusion pump (PicoPlus, Hayward). On the day of experiment perfusion rate was changed to 1.2 µL/minutes and allowed for 3 hours stabilization. After stabilization period, four basals were collected at 20 minutes intervals before dosing. Dialysate samples were collected in glass vials using CMA/170 refrigerated fraction collector.

Vehicle or NCE (3 mg/kg or 10 mg/kg) was administered by gavages after four fractions had been collected. The perfusate was collected until 6 hours after administration.

Acetylcholine concentrations in dialysate samples were measured by LC-MS/MS (API 4000, MDS SCIEX) method. Acetylcholine is quantified in the calibration range of 0.250 to 8.004 ng/mL in dialysates.

On completion of the microdialysis experiments, the animals were sacrificed and their brains were removed and stored in a 10% formalin solution. Each brain was sliced at 50µ on a cryostat (Leica) stained and examined microscopically to confirm probe placement. Data from animals with incorrect probe placement were discarded.

Microdialysis data were expressed as percent changes (Mean±S.E.M.) of baseline that was defined as the average absolute value (in fM/10 µL) of the four samples before drug administration.

Effects of NCE (3 & 10 mg/kg) and Vehicle treatments were statistically evaluated by one-way ANOVA followed by Dunnett's multiple comparison tests. In all statistical measures, a p<0.05 was considered significant. The Graph Pad Prism program statistically evaluated the data.

Example 59

Food Intake Measurement

Male Wister rats (120-140 gm) obtained from N. I. N. (National Institute of Nutrition, Hyderabad, India) was used. The chronic effect of the compounds of general formula (I) on food intake in well-fed rats was then determined as follows.

The rats were housed in single home cages for 28 days. During this period, the rats were either dosed orally or ip, with a composition comprising a compound of formula (1) or a corresponding composition (vehicle) without the said compound (control group), once a day, and the rat is provided with ad libitum food and water.

On 0, $1^{st}$, $7^{th}$, $14^{th}$, $21^{st}$ and $28^{th}$ day the rats were left with the pre-weighed amounts of food. Food intake and weight gain were measured on a routine basis. Also a food ingestion method is disclosed in the literature (Rask et al., European Journal of Pharmacology, 414, 2001, 215-224 and Turnball et. al., Diabetes, 2002, 51, 2441-2449, and some in-house modifications.). The respective parts of the descriptions are herein incorporated as a reference and they form part of the disclosure.

Some representative compounds have shown the statistically significant decrease in food intake, when conducted in the above manner at the doses of either 10 mg/Kg or 30 mg/Kg or both Example 60

Object Recognition Task Model

The cognition-enhancing properties of compounds of this invention were estimated using a model of animal cognition: the object recognition task model.

Male Wister rats (230-280 grams) obtained from N. I. N. (National Institute of Nutrition, Hyderabad, India) was used as experimental animals. Four animals were housed in each cage. Animals were kept on 20% food deprivation before one day and given water ad libitum throughout the experiment and maintained on a 12 hours light/dark cycle. Also the rats were habituated to individual arenas for 1 hour in the absence of any objects.

One group of 12 rats received vehicle (1 mL/Kg) orally and another set of animals received compound of the formula (I) either orally or i.p., before one hour of the familiar (T1) and choice trial (T2).

The experiment was carried out in a 50×50×50 cm open field made up of acrylic. In the familiarization phase, (T1), the rats were placed individually in the open field for 3 minutes, in which two identical objects (plastic bottles, 12.5 cm height×5.5 cm diameter) covered in yellow masking tape alone (a1 and a2) were positioned in two adjacent corners, 10 cm. from the walls. After 24 hours of the (T1) trial for long-term memory test, the same rats were placed in the same arena as they were placed in T1 trial. Choice phase (T2) rats were allowed to explore the open field for 3 minutes in presence of one familiar object (a3) and one novel object (b) (Amber color glass bottle, 12 cm high and 5 cm in diameter). Familiar objects presented similar textures, colors and sizes. During the T1 and T2 trial, explorations of each object (defined as sniffing, licking, chewing or having moving vibrissae whilst directing the nose towards the object at a distance of less than 1 cm) were recorded separately by stopwatch. Sitting on an object was not regarded as exploratory activity, however, it was rarely observed.

T1 is the total time spent exploring the familiar objects (a1+a2).

T2 is the total time spent exploring the familiar object and novel object (a3+b).

The object recognition test was performed as described by Ennaceur, A., Delacour, J., A new one-trial test for neurobiological studies of memory in rats—Behavioural data, Behay. Brain Res., 1988, 31, 47-59.

Some representative compounds have shown positive effects indicating the increased novel object recognition viz; increased exploration time with novel object and higher discrimination index.

| Example Number | Dose mg/kg, p.o. | Exploration time mean ± S.E.M (sec) | | Inference |
|---|---|---|---|---|
| 6. | 3 | 10.02 ± 1.54 | 15.27 ± 1.32 | Active |
| 8. | 3 | 6.72 ± 1.95 | 9.58 ± 2.26 | Active |
| 15. | 3 | 6.89 ± 1.54 | 13.26 ± 2.80 | Active |

Example 61

Water Maze

The water maze apparatus consisted of a circular pool (1.8 m diameter, 0.6 m high) constructed in black Perspex (TSE systems, Germany) filled with water (24±2° C.) and positioned underneath a wide-angled video camera to track animal. The 10 cm² perspex platform, lying 1 cm below the water surface, was placed in the centre of one of the four imaginary quadrants, which remained constant for all rats. The black Perspex used in the construction of the maze and platform offered no intramaze cues to guide escape behavior. By contrast, the training room offered several strong extramaze visual cues to aid the formation of the spatial map necessary for escape learning. An automated tracking system, [Videomot 2 (5.51), TSE systems, Germany] was employed. This program analyzes video images acquired via a digital camera and an image acquisition boards that determined path length, swim speed and the number of entries and duration of swim time spent in each quadrant of the water maze.

| Example Number | Scopolamine Induced Reversal |
|---|---|
| 6. | ≦3 mg/kg, p.o. |
| 8. | ≦3 mg/kg, p.o. |
| 15. | ≦3 mg/kg, p.o. |

Example 62

Chewing/Yawning/Stretching Induction by 5-HT$_6$ Antagonists

Male Wister rats weighing 200-250 grams were used. Rats were given vehicle injections and placed in individual, transparent chambers for 1 hour each day for 2 days before the test day, to habituate them to the observation chambers and testing procedure. On the test day, rats were placed in the observation chambers immediately after drug administration and observed continuously for yawning, stretching, and chewing behaviors from 60 to 90 minutes after drug or vehicle injections. 60 minutes prior to the drug administration Physostigramsine, 0.1 mg/kg i.p, was administered to all the animals. Average number of yawns, stretches and vacuous chewing movements during the 30 minutes observation period were recorded.

Reference: (A) King M. V., Sleight A., J., Woolley M. L., and et. al., Neuropharmacology, 2004, 47, 195-204. (B) Bentey J. C., Bourson A., Boess F. G., Fone K. C. F., Marsden C. A., Petit N., Sleight A. J., British Journal of Pharmacology, 1999, 126 (7), 1537-1542).

Example 63

Passive Avoidance

Animals were trained in a single-trial, step through, and light-dark passive avoidance paradigms. The training apparatus consisted of a chamber 300 mm in length, 260 mm wide, and 270 mm in height, constructed to established designs. The front and top were transparent, allowing the experimenter to observe the behaviour of the animal inside the apparatus. The chamber was divided into two compartments, separated by a central shutter that contained a small opening 50 mm wide and 75 mm high set close to the front of the chamber. The smaller of the compartments measured 9 mm in width and contained a low-power (6V) illumination source. The larger compartment measured 210 mm in width and was not illuminated. The floor of this dark compartment consisted of a grid of 16 horizontal stainless-steel bars that were 5 mm in diameter and spaced 12.5 mm apart. A current generator supplied 0.75 mA to the grid floor, which was scrambled once every 0.5 seconds across the 16 bars. A resistance range of 40-60 micro ohms was calculated for a control group of rats and the apparatus was calibrated accordingly. An electronic circuit detecting the resistance of the animal ensured an accurate current delivery by automatic variation of the voltage with change in resistance.

Experimental Procedure:

This was carried out as described previously. Adult male Wister rats weighing 200-230 grams were used. Animals were brought to the laboratory 1 hour before the experiment. On the day of training, animals were placed facing the rear of the light compartment of the apparatus. The timer was started once the animal has completely turned to face the front of the chamber. Latency to enter the dark chamber was recorded (usually <20 seconds) and having completely entered the dark compartment an inescapable foot shock of 0.75 mA for 3 seconds was administered to the animal. Animals were then returned to their home cages. Between each training session, both compartments of the chamber were cleaned to remove any confounding olfactory cues. Recall of this inhibitory stimulus was evaluated 24 hours, 72 hours and on 7 day post-training by returning the animal into the light chamber and recording their latency to enter the dark chamber, a criterion time of 300 seconds was employed.

Reference: (A) Callahan P. M., Rowe N. B., Tehim A., Abst. 776.19.2004, Society for neuroscience, 2004. (B) Fox G. B., Connell A. W. U., Murphy K. J., Regan C. M., Journal of Neurochemistry, 1995, 65, 6, 2796-2799.

We claim:

1. A compound of the general formula (I)

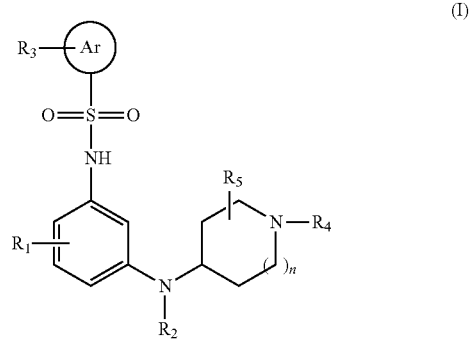

(I)

its stereoisomers, and its pharmaceutically acceptable salts, wherein $R_1$, $R_2$, $R_3$ and $R_5$ may be same or different and each independently represent hydrogen, halogen, ($C_1$-$C_3$)alkyl, ($C_1$-$C_3$)alkoxy, cyclo($C_3$-$C_6$)alkyl, cyclo($C_3$-$C_6$)alkoxy, halo($C_1$-$C_3$)alkyl or halo($C_1$-$C_3$)alkoxy;

represents aryl;
$R_4$ represents hydrogen, ($C_1$-$C_3$)alkyl, cyclo($C_3$-$C_6$)alkyl, halo($C_1$-$C_3$)alkyl, aryl or aralkyl;
"n" represents 1 to 2.

2. The compound as claimed in claim 1, which is selected from the group consisting of:
N-[4-Chloro-3-(1-methylpiperidin-4-ylamino)phenyl] benzenesulfonamide;

4-Fluoro-N-[4-Chloro-3-(1-methylpiperidin-4-ylamino)
  phenyl]benzenesulfonamide;
4-Methyl-N-[4-Chloro-3-(1-methylpiperidin-4-ylamino)
  phenyl]benzenesulfonamide;
4-Isopropyl-N-[4-Chloro-3-(1-methylpiperidin-4-
  ylamino)phenyl]benzenesulfonamide;
2-Bromo-N-[4-Chloro-3-(1-methylpiperidin-4-ylamino)
  phenyl]benzenesulfonamide;
4-Fluoro-N-[4-Methoxy-3-(1-methylpiperidin-4-
  ylamino)phenyl]benzenesulfonamide;
N-[4-Methoxy-3-(1-methylpiperidin-4-ylamino)phenyl]
  benzenesulfonamide;
2-Bromo-N-[4-Methoxy-3-(1-methylpiperidin-4-
  ylamino)phenyl]benzenesulfonamide;
4-Isopropyl-N-[4-Methoxy-3-(1-methylpiperidin-4-
  ylamino)phenyl]benzenesulfonamide;
4-Methyl-N-[4-Methoxy-3-(1-methylpiperidin-4-
  ylamino)phenyl]benzenesulfonamide;
2-Bromo-N-[3-(1-methylpiperidin-4-ylamino)phenyl]
  benzenesulfonamide;
4-Isopropyl-N-[3-(1-methylpiperidin-4-ylamino)phenyl]
  benzenesulfonamide;
4-Fluoro-N-[3-(1-methylpiperidin-4-ylamino)phenyl]
  benzenesulfonamide;
4-Methyl-N-[3-(1-methylpiperidin-4-ylamino)phenyl]
  benzenesulfonamide;
2-Bromo-N-[4-Methyl-3-(1-methylpiperidin-4-ylamino)
  phenyl]benzenesulfonamide;
N-[4-Methyl-3-(1-methylpiperidin-4-ylamino)phenyl]
  benzenesulfonamide;
4-Fluoro-N[4-Methyl-3-(1-Methylpiperidin-4-ylamino)
  phenyl]benzenesulfonamide;
4-Methyl-N-[4-Methyl-3-(1-Methylpiperidin-4-ylamino)
  phenyl]benzenesulfonamide;
N-[3-(1-methylpiperidin-4-ylamino)phenyl]benzene-
  sulfonamide;
N-[4-Chloro-3-(1-methylpiperidin-4-ylamino)phenyl]
  benzenesulfonamide hydrochloride;
4-Isopropyl-N-[4-Methyl-3-(1-Methylpiperidin-4-
  ylamino)phenyl]benzenesulfonamide hydrochloride;
2-Bromo-N-{4-methoxy-3-[N-methyl-N-(1-methyl pip-
  eridin-4-yl)amino]phenyl}benzenesulfonamide;
and its stereoisomers and its pharmaceutically acceptable
  salts.

3. A process for the preparation of compound of formula (I) as claimed in claim 1, which comprises
reacting a compound of formula (II),

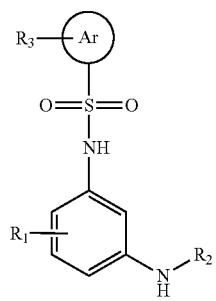

(II)

with piperidine-4-one derivatives, using a suitable reducing agent and base in presence of suitable solvent at ambient temperature to obtain a compound of formula (I), wherein all substitutions are as defined in claim 1.

4. A process for the preparation of compound of formula (I) as claimed in claim 1, which comprises
reacting a compound of formula (III),

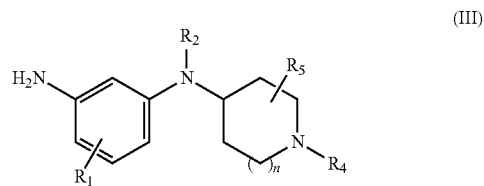

(III)

with aryl sulfonyl chloride derivatives, in presence of suitable solvent at ambient temperature to obtain a compound of formula (I), wherein all substitutions are as defined in claim 1.

5. A pharmaceutical composition comprising a pharmaceutically acceptable carrier, diluent, or excipient along with a therapeutically effective amount of a compound according to claims 1 or 2, its stereosisomers, its pharmaceutically acceptable salts, and any suitable combination of above.

6. A pharmaceutical composition as claimed in claim 5, which comprises one or more active ingredient selected from the group consisting of beta-secretase inhibitors; gamma-secretase inhibitors; amyloid aggregation inhibitors; directly or indirectly acting neuroprotective compounds; anti-oxidants; anti-inflammatory agents; 3-hydroxy-3-glutary-CoA (HMG-CoA) reductase inhibitors; acetylcholine-esterase inhibitors; N-methyl-D-aspartate (NMDA) receptor antagonists; α-amino-3-hydroxy-5-methyl-4-isoxazolepropionic acid (AMPA) agonists; compounds which modulate the release or concentration of neurotransmitters; compounds inducing the release of growth hormones; cannabinoid CB1 receptor antagonists or inverse agonists; antibiotic; phosphodiesterase-IV (PDE-IV) and phosphodiesterase-IX (PDE-IX) inhibitors, γ-aminobutyric acid$_A$ (GABA$_A$) inverse agonists; nicotinic agonists; histamine H3 antagonists; 5-hydroxytryptamine$_4$ (5-HT$_4$) agonists or partial agonists; 5-hydroxytryptamine$_6$ (5-HT$_6$) antagonists; a2-adrenoreceptor antagonists; muscarinic M1 agonists; muscarinic M2 antagonists; and metabotrophic glutamaic-receptor 5 positive modulators.

7. A pharmaceutical composition as claimed in claims 5 or 6, which comprises one or more additional agents selected from the group consisting of 3-APS, vitamin E, ginkgolide, donepezil, rivastigmine, tacrine, galantamine, memantine, NS-2330, ibutamoren mesylate, capromorelin, minocycline and rifampicin.

8. The pharmaceutical composition as claimed in claim 5, which is in the form of a tablet, capsule, powder, lozenges, suppositories, syrup, solution, suspension or an injectable, wherein said form is administered in a single dose or multiple dose units.

9. The pharmaceutical composition according to claim 5, for the treatment of Alzheimer's disease, depression, and schizophrenia.

10. A method for treating an individual having the disease selected from Alzheimer's disease, depression, and schizophrenia, which comprises the steps of providing to said individual a therapeutically effective amount of a compound of formula (I) as defined in claim 1.

11. A compound as claimed by claim 1, wherein said compound is radiolabeled.

* * * * *